United States Patent [19]
Hitz et al.

[11] Patent Number: 5,530,186
[45] Date of Patent: Jun. 25, 1996

[54] NUCLEOTIDE SEQUENCES OF SOYBEAN ACYL-ACP THIOESTERASE GENES

[75] Inventors: William D. Hitz; Narendra S. Yadav, both of Wilmington, Del.

[73] Assignee: E. I. Du Pont de Nemours and Company, Wilmington, Del.

[21] Appl. No.: 75,533

[22] PCT Filed: Dec. 16, 1991

[86] PCT No.: PCT/US91/09160

§ 371 Date: Jun. 14, 1993

§ 102(e) Date: Jun. 14, 1993

[87] PCT Pub. No.: WO92/11373

PCT Pub. Date: Sep. 7, 1992

Related U.S. Application Data

[63] Continuation-in-part of Ser. No. 631,264, Dec. 20, 1990, abandoned.

[51] Int. Cl.[6] .............................. A01H 5/00; C12N 15/29; C12N 15/82
[52] U.S. Cl. .................. 800/205; 435/172.3; 435/240.4; 536/23.6; 536/24.5; 800/DIG. 69
[58] Field of Search ................................. 536/23.6, 24.5; 800/205, DIG. 69; 435/172.3, 240.4

[56] References Cited

U.S. PATENT DOCUMENTS

| | | | |
|---|---|---|---|
| 4,394,443 | 7/1983 | Weissman et al. | 435/6 |
| 5,147,792 | 9/1992 | Perchorowicz et al. | 435/134 |
| 5,298,421 | 3/1994 | Davies et al. | 435/320.1 |
| 5,304,481 | 4/1994 | Davis et al. | 435/196 |
| 5,344,771 | 9/1994 | Davies et al. | 435/172.3 |

FOREIGN PATENT DOCUMENTS

| | | |
|---|---|---|
| 0255378 | 2/1988 | European Pat. Off. . |
| 0301749 | 2/1989 | European Pat. Off. ........ C12N 15/00 |
| 9012084 | 10/1990 | WIPO . |
| 9116421 | 10/1991 | WIPO . |

OTHER PUBLICATIONS

Mattson, F. H. et al, *Journal of Lipid Research*, 26, 194–202, 1985.
Grundy, S. M., *New England Journal of Medicine*, 314(12), 745–748, 1986.
Mensink, R. P. et al, *The Lancet*, 1, 122–125, 1987.
Keys, A., "Seven Countries: A Multivairate Analysis of Death of Coronary Heart Disease", Cambridge: Howard University Press, pp. 8–16, 67–79, 248–262, 333–335, 1980.
"Monounsaturates Use Said to Lower Several Major Risk Factors":, *Food Chemical News,* Mar. 2, 1987., p. 44.
Bayley, S. A. et al, *Biotechnology,* 6(10), 1219–1221, 1988.
Ohlrogge et al. "Molecular Strategies for Crop Improvement", *J. Cellular Biochem.* Suppl. 14E, 1990, UCLA Symposium on Molecular and Cellular Biology, p. 266 (Abstract RO19).
Goldberg et al. 1989 (Jan.) Cell 56:149–160.
van der Krol et al 1988 Gene 72: 45–50.
Chee et al 1989 Pl. Physiol 91: 1212–1218.
Christou et al 1989 (Oct.) Proc Natl Acad Sci USA 86: 7500–7504.
Hinchu et al 1988 Bio/Technology 6:915–922.
de Block et al 1989 Pl. Physiol 91:694–701.
Everett et al 1987 Bio/Technology 5:1201–1204.
Tanksley et al 1989 Bio/Technology 7: 257–264.
Harwood 1989 Critical Reviews in Pl. Sci. 8 (1): 1–43.
Bulose et al 1985 Journal Biol. Chem. 260 (29):15953–15958.
Randhawa et al 1987 Biochemistry 26: 1365–1373.
Slalsas et al 1990 Journal Exp. Botany 41 (Suppl.): P8–2 (Abstract P8.10).
Huhne et al 1990 Fat Sci. Technology 92 (6): 232–236.
Knauf 1987 Trends in Biotechnology 5: 40–47.
Battey 1989 Trends in Biotechnology 7: 122–126.
Bafar et al 1990 (Apr.) J of Amer. Oil Chemists Society 67:217–225.
Knauf et al 1990 J. Cell Biochem Supplement 14E: 266 (Abstract RO18).
McKean et al 1982 J. Biol Chem. 257: 12141–12147.
Murphy et al 1984 European J Biochem 142: 43–48.
Leto et al 1990 (May) Science 248:727–729.
Naggert et al 1988 J. Biol. Chem. 263: 1146–1150.

*Primary Examiner*—Patricia R. Moody

[57] ABSTRACT

The preparation and use of nucleic acid fragments encoding soybean seed acyl-ACP thioesterase enzyme or its precursor to modify plant oil composition are described. Chimeric genes incorporating such nucleic acid fragments and suitable regulatory sequences may be used to transform plants to control the levels of saturated and unsaturated fatty acids.

20 Claims, No Drawings

NUCLEOTIDE SEQUENCES OF SOYBEAN ACYL-ACP THIOESTERASE GENES

CROSS-REFERENCE TO RELATED APPLICATION

This application is a continuation-in-part of application U.S. Ser. No. 07/631,264, filed Dec. 20, 1990, now abandoned.

FIELD OF THE INVENTION

The invention relates to isolated nucleic acid fragments that encode plant seed acyl-ACP thioesterase enzymes or its precursor. Such fragments are useful in a method to alter plant oil composition.

BACKGROUND OF THE INVENTION

Soybean is the lowest-cost source of vegetable oil. Soybean oil accounts for about 70% of the 14 billion pounds of edible oil consumed in the United States and is a major edible oil worldwide. It is used in baking, frying, salad dressing, margarine, and a multitude of processed foods. Soybean is agronomically well-adapted to many parts of the U.S. In 1987/88 sixty million acres of soybean were planted in the U.S. Soybean products are also a major element of foreign trade since thirty million metric tons of soybeans, twenty-five million metric tons of soybean meal, and one billion pounds of soybean oil were exported in 1987/88. Nevertheless, increased foreign competition has lead to recent declines in soybean acreage and production in the U.S. The low cost and ready availability of soybean oil provides an excellent opportunity to upgrade this commodity oil into higher value speciality oils that add value to soybean crop for the U.S. farmer and enhance U.S. trade.

The specific performance and health attributes of edible oils are determined largely by their fatty acid composition. Soybean oil derived from commercial varieties is composed primarily of 11% palmitic (16:0), 4% stearic (18:0), 24% oleic (18:1), 54% linoleic (18:2) and 7% linolenic (18:3) acids. Palmitic and stearic acids are, respectively, 16- and 18-carbon-long, saturated fatty acids. Oleic, linoleic and linolenic are 18-carbon-long, unsaturated fatty acids containing one, two and three double bonds, respectively. Oleic acid is also referred to as a "monounsaturated" fatty acid, while linoleic and linolenic acids are also referred to as "polyunsaturated" fatty acids. The specific performance and health attributes of edible oils is determined largely by their fatty acid composition.

Soybean oil is high in saturated fatty acids when compared to other sources of vegetable oil and contains a low proportion of oleic acid relative to the total fatty acid content of the soybean seed. These characteristics do not meet important health needs as defined by the American Heart Association.

Recent research efforts have examined the role that monounsaturated fatty acid plays in reducing the risk of coronary heart disease. In the past, it was believed that monounsaturates, in contrast to saturates and polyunsaturates, had no effect on serum cholesterol and coronary heart disease risk. Several recent human clinical studies suggest that diets high in monounsaturated fat may reduce the "bad" (low-density lipoprotein) cholesterol while maintaining the "good" (high-density lipoprotein) cholesterol. (See Mattson, et al., Journal of Lipid Research (1985) 26:194–202). The significance of monounsaturated fat in the diet was confirmed by international researchers from seven countries at the Second Colloquium on Monounsaturated Fats sponsored by the National Heart, Lung and Blood Institutes in 1987.

Soybean oil is also relatively high in polyunsaturated fatty acids—at levels far in excess of essential dietary requirements. These fatty acids oxidize readily to give off-flavors and reduce the performance of unprocessed soybean oil. The stability and flavor of soybean oil is improved by hydrogenation, which chemically reduces the double bonds. However, this processing reduces the economic attractiveness of soybean oil.

A soybean oil low in total saturates and polyunsaturates and high in monounsaturate would provide significant health benefits to human consumers as well as economic benefit to oil processors. Such soybean varieties will also produce valuable meal for use as animal feed.

Another type of differentiated soybean oil is an edible fat for confectionary uses. More than two billion pounds of cocoa butter, the most expensive edible oil, are produced worldwide. The U.S. imports several hundred million dollars worth of cocoa butter annually. The high and volatile prices and uncertain supply of cocoa butter have encouraged the development of cocoa butter substitutes. The fatty acid composition of cocoa butter is 26% palmitic, 34% stearic, 35% oleic and 3% linoleic acids. Cocoa butter's unique fatty acid composition and distribution on the triglyceride molecule confer on it properties eminently suitable for confectionary end-uses: it is brittle below 27° C. and depending on its crystalline state, melts sharply at 25°–30° C. or 35°–36° C. Consequently, it is hard and non-greasy at ordinary temperatures and melts very sharply in the mouth. It is also extremely resistant to rancidity. For these reasons, a soybean oil with increased levels of palmitic and stearic acids, especially in soybean lines containing reduced levels of unsaturated fatty acids, is expected to provide a cocoa butter substitute in soybean. This will add value to oil and food processors as well as reduce the foreign import of certain tropical oils.

The partial purification of acyl-ACP thioesterase was reported from safflower seeds (McKeon et al., (1982) J. Biol. Chem. 257:12141–12147). However, this purification scheme was not useful for soybean, either because the thioesterases are different or because of the presence of other proteins such as the soybean seed storage proteins in seed extracts.

SUMMARY OF THE INVENTION

A method to alter the levels of saturated and unsaturated fatty acids in edible plant oils has been invented. Isolated soybean seed acyl-ACP thioesterase cDNAs for either the precursor or enzyme were used to create chimeric genes. Transformation of plants with the chimeric genes alters the fatty acid composition of the seed oil.

The invention is nucleic acid fragments comprising a nucleotide sequence encoding a plant acyl-ACP thioesterase. More specifically, the fragment may be isolated from soybean, oil producing Brassica species, *Cuphea viscosissima* or *Cuphea lanceolata*. One fragment of the invention corresponds to nucleotides 1 to 1602 of SEQ ID NO:1, or any nucleic acid fragment substantially homologous therewith. Another fragment corresponds to nucleotides 1 to 1476 of SEQ ID NO:3, or any nucleic fragment substantially homologous therewith. More preferred nucleic acid fragments are nucleotides 106 to 1206 of SEQ ID NO:1 and nucleotides 117 to 1217 of SEQ ID NO:3, or any nucleic acid fragment substantially homologous therewith for soybean seed acyl-ACP thioesterase precursor. Also more preferred nucleic acid fragments are nucleotides 271 to 1206 of SEQ ID NO:1 and nucleotides 282 to 1217 of SEQ ID NO:3, or any nucleic acid fragment substantially homologous therewith for mature soybean seed acyl-ACP thioesterase.

Another aspect of this invention is a chimeric gene capable of transforming a plant cell comprising a nucleic acid fragment encoding soybean seed acyl-ACP thioesterase cDNA operably linked to suitable regulatory sequences such that expression of the gene causes altered levels of acyl-ACP thioesterase in the seed. Preferred are those chimeric genes which incorporate nucleic acid fragments encoding soybean seed acyl-ACP thioesterase precursor or mature soybean seed acyl-ACP thioesterase enzyme.

A further aspect of this invention is a plant transformed with the chimeric genes described below.

Yet another embodiment of the invention is a method to produce seed oil containing altered levels of saturated and unsaturated fatty acids comprising: (a) transforming a plant cell with a chimeric gene described above, (b) growing sexually mature plants from the transformed plant cells, (c) screening progeny seeds from the sexually mature plants of step (b) for the desired levels of palmitic and stearic acid, and (d) processing the progeny seed to obtain oil containing altered levels of palmitic and stearic acid. Preferred plant cells and oils are soybean, oil producing Brassica species, sunflower, cotton, cocoa, peanut, safflower, and corn.

The invention is also embodied in a method of RFLP breeding to obtain altered levels of palmitic, stearic, and oleic acids in seed oil. This method comprises: (a) making a cross between two soybean varieties differing in the trait, (b) making a Southern blot of restriction enzyme-digested genomic DNA isolated from several progeny plants resulting from the cross of step (a); and (c) hybridizing the Southern blot with the radiolabeled nucleic acid fragments described herein.

BRIEF DESCRIPTION OF THE SEQUENCE DESCRIPTION

The invention can be more fully understood from the following detailed description and the Sequence Descriptions which form a part of this application. The Sequence Descriptions contain the three letter codes for amino acids as defined in 37 C.F.R. 1.822 which are incorporated herein by reference. The nucleotide sequences read from 5' to 3'.

SEQ ID NO:1 shows the 1602 nucleotides of a soybean seed acyl-ACP thioesterase cDNA.

SEQ ID NO:2 shows the amino acid sequence of the precursor protein of a soybean seed acyl-ACP thioesterase (the coding sequence of SEQ ID NO:1).

SEQ ID NO:3 shows the 1476 nucleotides of a soybean seed acyl-ACP thioesterase cDNA.

SEQ ID NO:4 shows the amino acid sequence of the precursor protein of a soybean seed acyl-ACP thioesterase (the coding sequence of SEQ ID NO:3).

SEQ ID NOs:5 and 6 show sequences related to the N-terminal sequence of acyl-ACP thioesterase.

SEQ ID NOs:7, 8 and 9 show respectively a protein sequence, DNA sequence and the related hybridization probe.

SEQ ID NOs:10, 11 and 12 show respectively a protein sequence, DNA sequence and the related hybridization probe.

SEQ ID NO:13 shows the sequence of the sequencing primer used to identify soybean acyl-ACP thioesterase isozymers.

SEQ ID NOs:14, 15, 16 and 17 also sequences chosen from SEQ ID NO:1 as probes for identification of acyl-ACP thioesterase genes from the *C. viscosissima C. lanceolata* genomes.

SEQ ID NO:18 shows a PCR primer corresponding to bases 83 through 117 in SEQ ID NO:1.

SEQ ID NO:19 shows a PCR primer corresponding to bases 274 through 296 in SEQ ID NO:1.

SEQ ID NO:20 shows an 1378 base pair, partial genomic clone of acyl-ACP thioesterase from *B. napus*.

SEQ ID NO:21 shows an 865 base pair insert sequenced from *C. viscosissima*.

SEQ ID NO:22 shows an 852 base pair insert sequenced from *C. lanceolata*.

DETAILED DESCRIPTION OF THE INVENTION

The present invention describes two isolated nucleic acid fragments that encode soybean seed acyl-ACP thioesterases. These enzymes catalyze the hydrolytic cleavings of palmitic acid, stearic acid and oleic acid from ACP in the respective acyl-ACPs.

Only recently have serious efforts been made to improve the quality of soybean oil through plant breeding, especially mutagenesis. A wide range of fatty acid composition have been discovered in experimental lines of soybean (Table 1). Findings from work on various oil crops suggest that the fatty acid composition of soybean oil can be significantly altered without affecting the agronomic performance of a soybean plant. However, there is no soybean mutant line with levels of saturates less than those present in commercial canola, the major competitor to soybean oil as a "healthy" oil.

TABLE 1

| Range of Fatty Acid Percentages Produced by Soybean Mutants | |
|---|---|
| Fatty Acids | Range of % |
| Palmitic Acid | 6–28 |
| Stearic Acid | 3–30 |
| Oleic Acid | 17–50 |
| Linoleic Acid | 35–60 |
| Linolenic Acid | 3–12 |

There are serious drawbacks to using mutagenesis to alter fatty acid composition. It is unlikely to discover mutations a) that result in a dominant ("gain-of-function") phenotype, b) in genes that are essential for plant growth, and c) in an enzyme that is not rate-limiting and that is encoded by more than one gene. Even when some of the desired mutations are available in soybean mutant lines their introgression also elite lines by traditional breeding techniques will be slow and expensive, since the desired oil compositions in soybean are most likely to involve several recessive genes.

Recent molecular and cellular biology techniques offer the potential for overcoming some of the limitations of the mutagenesis approach, including the need for extensive breeding. Particularly useful technologies are: a) seed-specific expression of foreign genes in transgenic plants (see Goldberg et al., (1989) Cell 56:149–160), b) use of antisense RNA to inhibit plant target genes in a dominant and tissue-specific manner (see van der Krol et al., (1988) Gene 72:45–50), c) use of homologous transgenes to suppress native gene expression (see Napoli et al., (1990) The Plant Cell 2:279–289; van der Krol et al., (1990) The Plant Cell 2:291–299; Smith et al., (1990) Mol. Gen. Genetics 224:447–481), d) transfer of foreign genes into elite commercial varieties of commercial oilcrops, such as soybean (Chee et al., (1989) Plant Physiol. 91:1212–1218; Christou et al., (1989) Proc. Natl. Acad. Sci. U.S.A. 86:7500–7504; Hinchee et al., (1988) Bio/Technology 6:915–922; EPO publication 0 301 749 A2), rapeseed (De Block et al., (1989) Plant Physiol. 91:694–701), and sunflower (Everett et al., (1987) Bio/Technology 5:1201–1204), and e) use of genes as restriction fragment length polymorphism (RFLP) markers in a breeding program, which makes introgression of recessive traits into elite lines rapid and less expensive (Tanksley et al. (1989) Bio/Technology 7:257–264). However, each of these technologies requires identification and isolation of commercially-important genes.

Oil biosynthesis in plants has been fairly well-studied (see Harwood (1989) in Critical Reviews in Plant Sciences, Vol. 8 (1):1–43). The biosynthesis of palmitic, stearic and oleic acids occurs in the plastids of plant cells by the interplay of three key enzymes of the "ACP track": palmitoyl-ACP elongase, stearoyl-ACP desaturase and acyl-ACP thioesterase.

Of these three enzymes, acyl-ACP thioesterase removes the acyl chain from the carrier protein (ACP) and thus from the metabolic pathway. The same enzyme, with slightly differing efficiency, catalyzes the hydrolysis of the palmitoyl, stearoyl and oleoyl-ACP thioesters. This multiple activity leads to substrate competition between enzymes and it is the competition of acyl-ACP thioesterase and palmitoyl-ACP elongase for the same substrate and of acyl-ACP thioesterase and stearoyl-ACP desaturase for the same substrate that leads to the production of a particular ratio of palmitic, stearic and oleic acids.

Once removed from the ACP track by the action of acyl-ACP thioesterase, fatty acids are exposed to the cytoplasm and there used to synthesize acyl-coenzyme A (CoA). These acyl-CoA's are the acyl donors for at least three different glycerol acylating enzymes (glycerol-3-P acyltransferase, 1-acyl-glycerol-3-P acyltransferase and diacylglycerol acyltransferase) which incorporate the acyl moieties into triacylglycerides during oil biosynthesis.

These acyltransferases show a strong, but not absolute, preference for incorporating saturated fatty acids at positions 1 and 3 and monounsaturated fatty acid at position 2 of the triglyceride. Thus, altering the fatty acid composition of the acyl pool will drive by mass action a corresponding change in the fatty acid composition of the oil. Furthermore, there is experimental evidence that, because of this specificity, given the correct composition of fatty acids, plants can produce cocoa butter substitutes (Bafor et al., (1990) J. Amer. Oil. Chemists Soc. 67:217–225).

Based on the above discussion, one approach to altering the levels of palmitic, stearic and oleic acids in vegetable oils is by altering their levels in the cytoplasmic acyl-CoA pool used for oil biosynthesis.

It should be possible to genetically modulate the competition both between palmitoyl-ACP elongase and acyl-ACP thioesterase and between stearoyl-ACP desaturase and thioesterase by modulating the expression level of thioesterase. While alteration of stearoyl-ACP desaturase activity either upward or downward may change the existing ratio of oleate:stearate and similarly altered expression of palmitoyl-ACP elongase might lead to new palmitate:(stearate+oleate) ratios, only modification of the acyl-ACP thioesterase activity is expected to change the amounts of both palmitate and stearate with one genetic manipulation. Increased competition leading to increased levels of palmitic and stearic acids would result from over-expression of cloned and re-introduced thioesterase genes which is the more proven technology, while decreased competition leading to decreased total saturated fatty acid would result from expression of antisense message from the acyl-ACP thioesterase gene. The simultaneous and opposite manipulation of the palmitoyl-ACP elongase and stearoyl-ACP desaturase activities would be required to achieve these same effects. There are thus two advantages to the use of nucleotide sequences encoding the acyl-ACP thioesterase to increase saturated fatty acid content in vegetable oil over the manipulation of the other two mentioned enzymes: 1) the manipulation does not require antisense technology and 2) both the palmitate and stearate levels should be elevated with one genetic manipulation.

Transfer of one or both of these nucleic acid fragments of SEQ ID NOs:1 and 3 of the invention or a part thereof that encodes a functional enzyme, with suitable regulatory sequences into a living cell will result in the production or over-production of acyl-ACP thioesterase, which may result in increased levels of palmitic and stearic acids in cellular lipids, including oil.

Transfer of the nucleic acid fragment or fragments of the invention, with suitable regulatory sequences that transcribe the present cDNA, into a plant having an endogenous seed acyl-ACP thioesterase substantially homologous with the present cDNA may inhibit by cosuppression the expression of the endogenous acyl-ACP thioesterase gene and, consequently, result in a decreased amount of palmitic and stearic acids in the seed oil (Jorgenson, Trends Biotech. (1990) 340–344).

Transfer of the nucleic acid fragment or fragments of the invention into a soybean plant with suitable regulatory sequences that transcribe the antisense RNA complementary to the mRNA, or its precursor, for seed acyl-ACP thioesterase may inhibit the expression of the endogenous acyl-ACP thioesterase gene and, consequently, result in reduced amounts of palmitic and stearic acids in the see oil.

The nucleic acid fragments of the invention can also be used as restriction fragment length polymorphism (RFLP) markers in soybean genetic studies and breeding programs.

DEFINITIONS

In the context of this disclosure, a number of terms shall be utilized. As used herein, the term "nucleic acid" refers to a large molecule which can be single stranded or double stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. As used herein, the term "homologous to" refers to the complementarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Hames and Higins (eds.) Nucleic Acid Hybridisation, IRL Press, Oxford, U.K. (1985)); or by the comparison of sequence similarity between two nucleic acids or proteins. As used herein, "substantially homologous" refers to nucleic acid molecules which require less stringent conditions of hybridization than those for homologous sequences, and coding DNA sequence which may involve base changes that do not cause a change in the encoded amino acid, or which involve base changes which may alter an amino acid, but not affect the functional properties of the protein encoded by the DNA sequence.

Thus, the nucleic acid fragments described herein include molecules which comprise possible variations of the nucleotide bases derived from deletion, rearrangement, random or controlled mutagenesis of the nucleic acid fragment, and even occasional nucleotide sequencing errors so long as the DNA sequences are substantially homologous.

"Gene" refers to a nucleic acid fragment that expresses a specific protein, including regulatory sequences preceding (5' non-coding) and following (4'non-coding) the coding region. "Acyl-ACP thioesterase gene" refers to a nucleic acid fragment that expresses a protein with acyl-ACP thioesterase activity. "Native" gene refers to the gene as found in nature with its own regulatory sequences. "Chimeric" gene refers to a gene that is comprised of heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is transcribed in the primary transcript but which is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to RNA transcript that include the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that may increase the efficacy of antisense RNA to block gene expression. "Ribozyme" refers to a catalytic RNA and includes sequence-specific endoribonucleases.

As used herein, "suitable regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. In artificial DNA constructs regulatory sequences can also control the transcription and stability of antisense RNA.

"Promoter" refers to a DNA sequence in a gene, usually upstream (5') to its coding sequence, which controls the expression of the coding sequence by providing the recognition for RNA polymerase and other factors required for proper transcription. In artificial DNA constructs promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The term "expression", as used herein, is intended to mean the production of a functional end-product. Expression or overexpression of the acyl-ACP thioesterase genes involves transcription of the gene and translation of the mRNA into precursor or mature acyl-ACP thioesterase proteins. "Antisense inhibition refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a transgene which has substantial homology to an endogenous gene resulting in the suppression of expression of both the ectopic and the endogenous gene.

"Altered expression" refers to the production of gene product(s) in transgenic organisms in amounts or proportions that differ significantly from that activity in comparable tissue (organ and of developmental type) from wild-type organisms.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Mature" protein refers to a functional acyl-ACP thioesterase enzyme without its transmit peptide. "Precursor" protein refers to the mature protein with a native or foreign transit peptide. "Transit" peptide refers to the amino terminal extension of a polypeptide, which is translated in conjunction with the polypeptide forming a precursor peptide and which is required for its uptake by plastids of a cell.

"Transformation" herein refers to the transfer of a foreign gene into the genome of a host organism and its genetically stable inheritance. "Restriction fragment length polymorphism" refers to different sized restriction fragment lengths due to altered nucleotide sequences in or around variant forms of genes. "Fertile" refers to plants that are able to propagate sexually.

"Oil producing species" herein refers to plant species which produce and store triacylglycerol in specific organs, primarily in seeds. Such species include soybean, canola, sunflower, cotton, cocoa, peanut, safflower and corn. The group also includes non-agronomic species which are useful in developing appropriate expression vectors such as tobacco and *Arabidopsis thaliana*, and wild species which may be a source of unique fatty acids.

Purification of Soybean Seed Acyl-ACP Thioesterase

In order to modulate the activity of acyl-ACP thioesterase in the seed, it is essential to isolate or purify the complete gene(s) or cDNA(s) encoding the target enzyme(s).

Acyl-ACP thioesterase proteins were purified to a protein mixture containing either two or three peptides when analyzed by SDS polyacrylamide gel electrophoresis (SDS-PAGE) starting from the soluble fraction of extracts made from developing soybean seeds following binding to DEAE-cellulose, ammonium sulfate precipitation, chromatographic separation on blue sepharose, high performance anion exchange, alkyl-ACP sepharose, and phenyl-Superose. In a typical preparation, the fold purification of thioesterase activity was about 8500. The preparation runs as a single band in native polyacrylamide gel electrophoresis, and as a single, symmetrical peak in gel filtration chromatography indicating a native molecular weight of about 75 kD. SDS-PAGE of these preparations showed a very minor peptide of about 39 kD and two major peptides at about 33 and 34 kD.

Polyclonal antibodies raised to each of these peptides individually in mice cross-reacted in all combinations upon Western analysis indicating that the peptides are antigenically very similar. All attempts at separating these three peptides with retention of thioesterase activity failed. The peptides at 33 and 34 kD could be separated from the 39 kD peptide by reverse phase chromatography on a diphenyl matrix. The mixture containing these two peptides was analyzed by N-terminal amino acid sequencing and one main sequence of the following amino acid order was found:

Arg—Val—Glu—Ala—Pro—Gly—Gly—Thr—Leu—Ala—Asp—Arg—Leu
(SEQ ID NO:5).

These results lead to the conclusion that the native thioesterase enzyme is a heterodimer of at least three polypeptides with similar amino acid sequences and nearly identical N-termini. Whether the mixture arises as the result of the expression of slightly dissimilar genes or as the result of heterogenous proteolytic processing at the carboxyl terminal of the product of one gene of or identical genes is not known.

Cloning of Soybean Seed Acyl-ACP Thioesterase cDNA

The combined 33 and 34 kD peptides from reversed phase purification were denatured and reduced with dithiothreitol (DTT), the alkylated with vinyl pyridine. The derivatized protein was desalted, lyophilized and subjected to DNBr cleavage in 70% trifluoroacetic acid (TFA) solution. Peptide fragments produced by DNBr were separated by SDS-PAGE electophoresis, electrophoretically transferred onto Immobilon®-P membrane and stained with non-acid Coomassie blue. Three main peptides of 28, 16 and 14 kD were observed and cut from the blot of N-terminal sequencing. Of these, the peptide of 14 kD gave the following amino acid sequence from its N-terminal:

Ile—Glu—Ile—Tyr—Lys—Tyr—Pro—Ala—Trp—Leu—Asp—Ile—Val—Glu—Ile
(SEQ ID NO:6).

Based on this sequence from the first Ile to the first two bases of the codon for the last Ile, a set of eight degenerate 41 nucleotide-long oligonucleotides was synthesized. The design took into account the codon usage in selected soybean seed genes and used six deoxyinosines at positions of ambiguity. The probe, following radiolabeling, was used to screen a cDNA expression library made in Lambda Zap vector from polyA$^+$ RNA from 20-day-old developing soybean seeds. Five positively hybridizing plaques were subjected to plaque purification. Sequences of the pBluescript (Stratagene) vector, including the cDNA inserts, from each of the purified phage stocks were excised in the presence of a helper phase and the resultant phagemids used to infect *E. coli* cells resulting in double-stranded plasmids, p22A, p22B, p23A, p25A, and p25B.

The cDNA insert in plasmid p22B is flanked at both ends by the two EcoRI sites introduced by the cDNA construction and its cloning into the vector pBluescript. The nucleotide sequence of the cDNA insert in p22B encodes a 367 amino acid open reading frame that includes the N-terminal sequence found in the purified protein at the fifty-sixth amino acid of the open reading frame. Thus the first fifty-five amino acids are presumably the transit peptide required for import of the precursor protein into the plastid. The methionine codon at base number 106 of p22B is the apparent start methionine since a) it is the first methionine after the last stop codons 5' to the inframe with the N-terminal sequence and, b) the N-terminal methionine in all but one known chloroplast transit peptides is followed by alanine. Thus, it can be deduced that the acyl-ACP thioesterase precursor protein encoded by this gene consists of fifty-five amino acid transitpeptide and a 312 amino acid mature protein before any further proteolytic processing occurs. A fusion protein comprising the first sixteen amino acids of β-galactosidase, and beginning at the fourth amino acid of the mature soybean seed acyl-ACP thioesterase in an appropriate plasmid is expressed in *E. coli* and is catalytically functional.

The entire cDNA insert in p22B was cut from the Bluescript plasmid, radiolabeled and used as a probe for additional thioesterase genes in the soybean seed cDNA library. Five additional clones were characterized. Of these, one is identical to clone 22B from one hundred bases before the stop codon of the open reading frame and through the 3' non-coding region. The other four appear to be identical to each other, but differ from 22b. One of these clones (4C) was sequenced completely and is shown in SEQ ID NO:3. The open reading frame on the cDNA encodes a thioesterase precursor protein which is again 367 amino acids in length and which, at the amino acid level, is 97% identical to the thioesterase encoded by insert 22B. Both the 5' and 3' non-coding sequences of the two genes diverge in identity as the distance from the open reading frame increases.

The fragments of the instant invention may be used, if desired, to isolate substantially homologous acyl-ACP thioesterase cDNAs and genes, including those from plant species other than soybean. Isolation of homologous genes is well-known in the art. Southern blot analysis reveals that the soybean cDNA for the enzyme hybridizes to several different-sized DNA fragments in the genomic DNA of tomato, rapeseed (Brassica napus), soybean, sunflower and Arabidopsis (which has a very simple genome). Although the number of different genes or "pseudogenes" (non-functional genes) present in any plant is unknown, it is expected to be more than one since acyl-ACP thioesterase is an important enzyme. Moreover, plants that are amphidiploid (that is, derived from two progenitor species), such as soybean, rapeseed (B. napus), and tobacco will have genes from both progenitor species.

Overexpression of the Enzyme in Transgenic Species

The nucleic acid fragment of the instant invention encoding soybean seed acyl-ACP thioesterase cDNA, or a coding sequence derived from other cDNAs or genes for the enzyme, with suitable regulatory sequences, can be used to overexpress the enzyme in transgenic soybean as well as other transgenic species. Such a recombinant DNA construct may include either the native acyl-ACP thioesterase gene or a chimeric gene. One skilled in the art can isolate the coding sequences from the fragment of the invention by using and/or creating sites for restriction endonucleases, as described Sambrook et al. Molecular Cloning: A Laboratory Manual, 2nd Ed. (1989), Cold Spring Harbor Laboratory Press. Of particular utility are sites for Nco I (5'-CCATGG-3') and Sph I (5'-GCATGC-3') that allow precise removal of coding sequences starting with the initiating codon ATG. For isolating the coding sequence of acyl-ACP thioesterase precursor from the fragment of invention, an Nco I site can be engineered by substituting nucleotide A at position 105 with C. Cutting at this engineered site (or alternatively at an existing Hind III (5'-AAGCTT-3') site beginning at base pair 93 of p22B) along with cuts at restriction endonuclease sites near the 3' end of p22B such as the Spi I at 1339 or the Xmn I site at 1562 allows removal of the fragment encoding the acyl-ACP thioesterase precursor protein and directional reinsertion into a properly designed vector.

Inhibition of Plant Target Genes by Use of Antisense DNA

Antisense RNA has been used to inhibit plant target genes in a dominant and tissue-specific manner (see van der Krol et al., Gene (1988) 72:45–50; Ecker et al., Proc. Natl. Acad. Sci. U.S.A. (1986) 83:5372–5376; van der Krol et al., Nature (1988) 336:866–869; Smith et al., Nature (1988) 334:724–726; Sheehy et al., Proc. Natl. Acad. Sci. U.S.A. (1988) 85:8805–8809; Rothstein et al., Proc. Natl. Acad. Sci. U.S.A. (1987) 84:8439–8443; Cornelissen et al., Nucl. Acids Res. (1988) 17:833–843; Cornelissen, Nucl. Acid Res. (1989) 17:7203–7209; Robert et al., Plant Mol. Biol. (1989) 13:399–409; Cannon et al., Plant Molec. Biol. (1990) 15:39–47).

The use of antisense inhibition of the seed enzyme would require isolation of the coding sequence for genes that are expressed in the target tissue of the target plant. Thus, it will be more useful to use the fragment of the invention to screen seed-specific cDNA libraries, rather than genomic libraries or cDNA libraries from other tissues, from the appropriate plant for such sequences. Moreover, since there may be more than one gene encoding seed acyl-ACP thioesterase, it may be useful to isolate the coding sequences from the other genes from the appropriate crop. The genes that are most highly expressed are the best targets for antisense inhibition. The level of transcription of different genes can be studied by known techniques, such as nuclear run-off transcription.

There have been examples of using the entire cDNA sequence for antisense inhibition (Sheehy et al., Proc. Natl. Acad. Sci. U.S.A. (1988) 85:8805–8809). Thus, for expressing antisense RNA in soybean seed from the fragment of the invention, the entire fragment of the invention (that is, the entire cDNA for soybean seed acyl-ACP thioesterase within the restriction sites described above) may be used. There is also evidence that the 3' non-coding sequences can play an important role in antisense inhibition (Ch'ng et al., Proc. Natl. Acad. Sci. U.S.A. (1989) 86:10006–10010) or short fragments of 5' coding sequence (as few as 41 base-pairs of a 1.87 kb cDNA) (Cannon et al., Plant Molec. Biol. (1990) 15:39–47). Thus, for expressing antisense RNA in soybean seed from the fragment of the invention, a small fragment of the invention, consisting of at least 41 base pairs of the acyl-ACP thioesterase cDNA, may also be used.

Inhibition of Plant Target Genes by Cosuppression

The phenomenon of cosuppression has also been used to inhibit plant target genes in a dominant and tissue-specific manner (Napoli et al., The Plant Cell (1990) 2:279–289; van der Krol et al., The Plant Cell (1990) 2:291–299; Smith et al., Mol. Gen. Genetics (1990) 224: 447–481). The nucleic acid fragment of the instant invention encoding soybean seed acyl-ACP thioesterase cDNA, or a coding sequence derived from other cDNAs or genes for the enzyme, along with suitable regulatory sequences, can be used to reduce the level of the enzyme in a transgenic oilseed plant which contains an endogenous gene substantially homologous to the introduced acyl-ACP thioesterase cDNA. The experimental procedures necessary for this are similar to those described above for sense overexpression of the acyl-ACP thioesterase cDNA. Cosuppressive inhibition of an endogenous gene using the entire cDNA sequence (Napoli et al., The Plant Cell (1990) 2:279–289; van der Krol et al., The Plant Cell (1990) 2:291–299) and also using part of a gene (730 bp of a 1770 bp cDNA) (Smith et al., Mol. Gen. Genetics (1990) 224:477–481) are known. Thus, all or part of the nucleotide sequence of the present acyl-ACP thioesterase cDNA may be used to reduce the levels of acyl-ACP thioesterase enzyme in a transgenic oilseed.

Selection of Hosts, Promoters and Enhancers

A preferred class of heterologous hosts for the expression of the coding sequence of acyl-ACP thioesterase precursor or the antisense RNA are eukaryotic hosts, particularly the cells of higher plants. Particularly preferred among the higher plants are the oilcrops, such as soybean (*Glycine max*), rapeseed (*Brassica napus, B. campestria*), sunflower (*Helianthus annus*), cotton (*Gossypium hirautum*), corn (*Zea mays*), cocoa (*Theobroma cacao*), and peanut (*Arachis hypogaea*). Expression in plants will use regulatory sequences functional in such plants.

The expression of foreign genes in plants is well-established (De Blaere et al., Meth. Enzymol. (1987) 153:277–291). The origin of promoter chosen to drive the expression of the coding sequence or the antisense RNA is not critical provided it has sufficient transcriptional activity to accomplish the invention by increasing or decreasing, respectively, the level of translatable mRNA for acyl-ACP thioesterase in the desired host tissue. Preferred promoters include (a) strong constitutive plant promoters, such as those directing the 19S and 35S transcripts in Cauliflower mosaic virus (Odell et al., Nature (1985) 313:810–812; Hull et al., Virology (1987) 86:482–493), and (b) tissue- or developmentally-specific promoters. Examples of tissue-specific promoters are the light-inducible promoter of the small subunit of ribulose 1,5-bis-phosphate carboxylase if expression is desired in photosynthetic tissues, maize zein protein (Matzke et al., EMBO J. (1984) 3:1525), and chlorophyll a/b binding protein (Lampa et al., Nature (1986) 316:750–752).

Particularly preferred promoters are those that allow seed-specific expression. This may be especially useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., Ann. Rev. Plant Physiol. (1984) 35:191–221; Goldberg et al., Cell (1989) 56:149–160). Moreover, different seed storage proteins may be expressed at different stages of seed development.

Expression of seed-specific genes has been studied in great detail (See reviews by Goldberg et al., Cell (1989) 56:149–160 and Higgins et al., Ann. Rev. Plant Physiol. (1984) 35:191–221). There are currently numerous examples for seed-specific expression of seed storage protein genes in transgenic dicotyledonous plants. These include genes from dicotyledonous plants for bean β-phaseolin (Sengupta-Gopalan et al., Proc. Natl. Acad. Sci. U.S.A. (1985) 82:3320–3324; Hoffman et al., Plant Mol. Biol. (1988) 11:717–729), bean lectin (Voelker et al., EMBO J. (1987) 6:3571–3577), soybean lectin (Okamuro et al., Proc. Natl. Acad. Sci. U.S.A. (1986) 83:8240–8244), soybean Kunitz trypsin inhibitor (Perez-Grau et al., Plant Cell (1989) 1:095–1109), soybean β-conglycinin (Beachy et al., EMBO J. (1985) 4:3047–3053; pea vicilin (Higgins et al., Plant Mol. Biol. (1988) 11:683–695), pea convicilin (Newbigin et al., Plants (1990) 180:461), pea legumin (Shirsat et al., Mol. Gen. Genetics (1989) 215:326); rapeseed napin (Radke et al., Theor. Appl. Genet. (1988) 75:685–694) as well as genes from monocoytledonous plants such as for maize 15 kD zein (Hoffman et al., EMBO J. (1987) 6:3213–3221), maize 18 kD oleosin (Lee et al., Proc. Natl. Acad. Sci. U.S.A. (1991) 888:6181–6185), barley β-hordein (Marris et al., Plant Mol. Biol. (1988) 10:359–366) and wheat glutenin (Colot et al., EMBO J. (1987) 6:3559–3564). Moreover, promoters of seed-specific genes operably linked to heterologous coding sequences in chimeric gene constructs also maintain their temporal and spatial expression pattern in transgenic plants. Such examples include *Arabidopsis thaliana* 2S seed storage protein gene promoter to express enkephalin peptides in Arabidopsis and *B. napus* seeds (Vandekerckhove et al., Bio/Technology (1989) 7:929–932), bean lectin and bean β-phaseolin promoters to express luciferase (Riggs et al., Plant Sci. (1989) 63:47–57), and wheat glutenin promoters to express chloramphenicol acetyl transferase (Colot et al., EMBO J. (1987) 6:3559–3564).

Of particular use in the expression of the nucleic acid fragment of the invention will be the heterologous promoters from several soybean seed storage protein genes such as those for the Kunitz trypsin inhibitor (Jofuku et al., Plant Cell (1989) 1:1079–1093; glycinin (Nielson et al., Plant Cell (1989) 1:313–328), and β-conglycinin (Harada et al., Plant Cell (1989) 1:415–425). Promoters of genes for α- and β-subunits of soybean β-conglycinin storage protein will be particularly useful in expressing the mRNA or the antisense RNA to acyl-ACP thioesterase in the cotyledons at mid- to late-stages of seed development (Beachy et al., EMBO J. (1985) 4:3047–3053 in transgenic plants. This is because there is very little position effect on their expression in transgenic seeds, and the two promoters show different temporal regulation. The promoter for the α-subunit gene being expressed a few days before that for the β-subunit gene. This is important for transforming rapeseed where oil biosynthesis begins about a week before seed storage protein synthesis (Murphy et al., J. Plant Physiol. (1989) 135:63–69).

Also of particular use will be promoters of genes expressed during early embryogenesis and oil biosynthesis. The native regulatory sequences, including the native promoter, of the acyl-ACP thioesterase gene expressing the nucleic acid fragment of the invention can be used following its isolation by those skilled in the art. Heterologous promoters from other genes involved in seed oil biosynthesis, such as those for *B. napus* isocitrate lyase and malate synthase (Comai et al., Plant Cell (1989) 1:293–300), Arabidopsis ACP (Post-Beittenmiller et al., Nucl. Acids Res. (1989) 17:1777), *B. napus* ACP (Safford et al., Eur. J. Biochem. (1988) 174:287–295), *B. campestris* ACP (Rose et al., Nucl. Acids Res. (1987) 15:7197), and *Zea mays* oleosin (Lee et al., Proc. Natl. Acad. Sci. U.S.A. (1991) 88:6181–6185) may also be used. The genomic DNA sequence for *B. napus* oleosin is also published (Lee et al., Plant Physiol. (1991) 96:1395–1397) and one skilled in the art can use this sequence to isolate the corresponding promoter. The partial protein sequences for the relatively-abundant enoyl-ACP reductase and acetyl-CoA carboxylase are published (Slabas et al., Biochim. Biophys. Acta (1987) 877:271–280; Cottingham et al., Biochim. Biophys. Acta (1988) 954:201–207) and one skilled in the art can use these sequences to isolate the corresponding seed genes with their promoters.

Attaining the proper level of expression of acyl-ACP thioesterase mRNA or antisense RNA may require the use of different chimeric genes utilizing different promoters. Such chimeric genes can be transferred into host plants either together in a single expression vector or sequentially using more than one vector.

It is envisioned that the introduction of enhancers or enhancer-like elements into either the native acyl-ACP thioesterase promoter or into other promoter constructs will also provide increased levels of primary transcription for antisense RNA or in RNA for acyl-ACP thioesterase to accomplish the inventions. This would include viral enhancers such as that found in the 35S promoter (Odell et al., Plant Mol. Biol. (1988) 10:263–272), enhancers from the opine genes (Fromm et al., Plant Cell (1989) 1:977–984), or enhancers from any other source that result in increased transcription when placed into a promoter operably linked to the nucleic acid fragment of the invention.

Of particular importance is the DNA sequence element isolated from the gene for the α-subunit of β-conglycinin that can confer 40-fold seed-specific enhancement to a constitutive promoter (Chen et al., Dev. Genet. (1989) 10:112–122). One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

The invention can also be accomplished by a variety of other methods to obtain the desired end. In one form, the invention is based on modifying plants to produce increased levels of acyl-ACP thioesterase by virtue of having significantly larger numbers of copies of the acyl-ACP thioesterase gene product. This may result in sufficient increases in acyl-ACP thioesterase activity levels to accomplish the invention.

Any 3' non-coding region capable of providing a polyadenylation signal and other regulatory sequences that may be required for the proper expression of the acyl-ACP thioesterase coding region can be used to accomplish the invention. This would include the native 3' end of the substantially homologous soybean acyl-ACP thioesterase gene(s), the 3' end from a heterologous acyl-ACP thioesterase, the 3' end from viral genes such as the 3' end of the 35S or the 19S cauliflower mosaic virus transcripts, the 3' end from the opine synthesis genes, the 3' ends of ribulose 1,5-biphosphate carboxylase or chlorophyll a/b binding protein, or 3' end sequences from any source such that the sequence employed provides the necessary regulator information within its nucleic acid sequence to result in the proper expression of the promoter/acyl-ACP thioesterase coding region combination to which it is operably linked. There are numerous examples in the art that teach the usefulness of different 3' non-coding regions.

Transformation Methods

Various methods of transforming cells of higher plants according to the present invention are available to those skilled in the art (see EPO Pub. 0 295 959 A2 and 0 318 341 A1). Such methods includes those based on transformation vectors based on the Ti and Ri plasmids of *Agrobacterium spp*. It is particularly preferred to use the binary type of these vectors. Ti-derived vectors transform a wide variety of higher plants, including monocotyledonous and dicotyledonous plants, Sukhapinda et al., Plant Mol. Biol. (1987) 8:209–216; Potrykus, Mol. Gen. Genet. (1985) 199:183). Other transformation methods are available to those skilled in the art, such as direct uptake of foreign DNA constructs (see EPO Pub. 0 295 959 A2), techniques of electroporation (Fromm et al., Nature (1986) (London) 319:791) or high-velocity ballistic bombardment with metal particles coated with the nucleic acid constructs (Kline et al., Nature (1987) (London) 327:70). Once transformed, the cells can be regenerated by those skilled in the art.

Of particular relevance are the recently described methods to transform foreign genes into commercially important crops, such as rapeseed (De Block et al., Plant Physiol. (1989) 91:694–701), sunflower (Everett et al., Bio/Technology (1987) 5:1201), and soybean (Christou et al., Proc. Natl. Acad. Sci U.S.A. (1989) 86:7500–7504) and corn (Fromm et al., (1990) Bio/technology 8:833–839).

Application to RFLP Technology

The use of restriction fragment length polymorphism (RFLP) markers in plant breeding has been well-documented in the art (Tanksley et al., Bio/Technology (1989) 7:257–264). The nucleic acid fragment of the invention indicates two gene copies by Southern blotting. Both of these have been mapped on a soybean RFLP map (Tingey et al., J. Cell Biochem. (1990), Supplement 14E p. 291, abstract R153) and can be used as RFLP markers for traits linked to these mapped loci. These traits will include altered levels of palmitic, stearic and oleic acid. The nucleic acid fragment of the invention can also be used to isolate the acyl-ACP thioesterase gene from variant (including mutant) soybeans with altered stearic acid levels. Sequencing of these genes will reveal nucleotide differences from the normal gene that cause the variation. Short oligonucleotides designed around these differences may be used as hybridization probes to follow the variation in stearic, palmitic and oleic acids. Oligonucleotides based on differences that are linked to the variation may be used as molecular markers in breeding these variant oil traits.

EXAMPLE 1

ISOLATION OF cDNA FOR SOYBEAN SEED ACYL-ACP THIOESTERASE

PREPARATION OF RADIOLABELED PALMITOYL, STEAROYL AND OLEOYL-ACP

Purification of Acyl Carrier Protein (ACP) from *E. coli*

To frozen *E. coli* cell paste, (0.5 kg of ½ log phase growth of *E. coli* B grown on minimal media and obtained from Grain Processing Corp, Muscatine, Iowa) was added 50 mL of a solution 1M in Tris, 1M in glycine, and 0.25M in EDTA. Ten mL of 1M $MgCl_2$ was added and the suspension was thawed in a water bath at 50° C. As the suspension approached 37° C. it was transferred to a 37° C. bath, made to 10 mM in 2-mercaptoethanol and 20 mg of DNAse and 50 mg of lysozyme were added. The suspension was stirred for 2 h, then sheared by three 20 sec bursts in a Waring Blendor. The volume was adjusted to 1 L and the mixture was centrifuged at 24,000 xg for 30 min. The resultant supernatant was centrifuged at 90,000 xg for 2 h. The resultant high-speed pellet was saved for extraction of acyl-ACP synthase (see below) and the supernatant was adjusted to pH 6.1 by the addition of acetic acid. The extract was then made to 50% in 2-propanol by the slow addition of cold 2-propanol to the stirred solution at 0° C. The resulting precipitate was allowed to settle for 2 h and then removed by centrifugation at 16,000 xg. The resultant supernatant was adjusted to pH 6.8 with KOH and applied at 2 mL/min to a 4.4×12 cm column of DEAE-Sephacel which had been equilibrated in 10 mM MES, pH 6.8. The column was washed with 10 mM MES, pH 6.8 and eluted with 1 L of a gradient of LiCl from 0 to 1.7M in the same buffer. Twenty mL fractions were collected and the location of eluted ACP was determined by applying 10 μL of every second fraction to a lane of a native polyacrylamide (20% acrylamide) gel electrophoresis (PAGE). Fractions eluting at about 0.7M LiCl contained nearly pure ACP and were combined, dialyzed overnight against water and then lyophilized.

Purification of Acyl-ACP Synthase

Membrane pellets resulting from the high-speed centrifugation described above were homogenized in 380 mL of 50 mM Tris-Cl, pH 8.0, and 0.5M in NaCl and then centrifuged at 80,000 xg for 90 min. The resultant supernatant was discarded and the pellets resuspended in 50 mM Tris-Cl, pH 8.0, to a protein concentration of 12 mg/mL. The membrane suspension was made to 2% in Triton X-100 and 10 mM in $MgCl_2$, and stirred at 0° C. for 20 min before centrifugation at 80,000 xg for 90 min. The protein in the resultant supernatant was diluted to 5 mg/mL with 2% Triton X-100 in 500 mM Tris-Cl, pH 8.0 and, then, made to 5 mM ATP by the addition of solid ATP (disodium salt) along with an equimolar amount of $NaHCO_3$. The solution was warmed in a 55° C. bath until the internal temperature reached 53° C. and was then maintained at between 53° C. and 55° C. for 5 min. After 5 min the solution was rapidly cooled on ice and centrifuged at 15,000 xg for 15 min. The supernatant from the heat treatment step was loaded directly onto a column of 7 mL Blue Sepharose 4B which had been equilibrated in 50 mM Tris-Cl, pH 8.0, and 2% Triton X-100. The column was washed with 5 volumes of the loading buffer, then 5 volumes of 0.6M NaCl in the same buffer and the activity was eluted with 0.5M KSCN in the same buffer. Active fractions were assayed for the synthesis of acyl-ACP, as described below, combined, and bound to 3 mL settled-volume of hydroxylapatite equilibrated in 50 mM Tris-Cl, pH 8.0, 2% Triton X-100. The hydroxylapatite was collected by centrifugation, washed twice with 20 mL of 50 mM Tris-Cl, pH 8.0, 2% Triton X-100. The activity was eluted with two 5 mL washes of 0.5M potassium phosphate, pH 7.5, 2% Triton X-100. The first wash contained 66% of the activity and it was concentrated with a 30 kD membrane filtration concentrator (Amicon) to 1.5 mL.

Synthesis of Radiolabeled Acyl-ACP

A solution of [$^3$H] palmitic acid, [$^{14}$C]-stearic acid and [$^{14}$C]-oleic acid (120 mmol each) prepared in methanol were dried in a glass reaction vial. The ACP preparation described above (1.15 mL, 32 nmol) was added along with 0.1 mL of 0.1M ATP, 0.05 mL of 80 mM DTT, 0.1 mL of 8M LiCl, and 0.2 mL of 13% Triton X-100 in 0.5M Tris-Cl, pH 8.0, with 0.1M $MgCl_2$. The reaction was mixed thoroughly and 0.3 mL of the acyl-ACP synthase preparation was added and the reaction was incubated at 37° C. After 0.5 h intervals a 10 μL aliquot was taken and dried on a small filter paper disc. The disc was washed extensively with chloroform:methanol:acetic acid (8:2:1, v:v:v) and radioactivity retained on the disc was taken as a measure of stearoyl-ACP. At 2 h about 88% of the ACP had been consumed. The reaction mixes were diluted 1 to 4 with 20 mM Tris-Cl, pH 8.0, and applied to 1 mL DEAE-Sephacel columns equilibrated in the same buffer. The columns were washed in sequence with 5 mL of 20 mM Tris-Cl, pH 8.0, 5 mL of 80% 2-propanol in 20 mM Tris-Cl, pH 8.0, and eluted with 0.5M LiCl in 20 mM Tris-Cl, pH 8.0. The column eluates were passed directly onto 3 mL columns of octyl-sepharose CL-4B which were washed with 10 mL of 20 mM potassium phosphate, pH 6.8, and then eluted with 35% 2-propanol in 2 mM potassium phosphate, pH 6.8. The eluted products were lyophilized and redissolved at a concentration of 24 μM.

PREPARATION OF ALKYL-ACP AFFINITY COLUMN

Synthesis of N-hexadecyliodoacetamide

1-Hexadecylamide (3.67 mmol) was dissolved in 14.8 mL of $CH_2Cl_2$, cooled to 4° C., and 2.83 mmol of iodoacetic anhydride in 11.3 mL of $CH_2Cl_2$ was added dropwise to the stirred solution. The solution was warmed to room temperature and held for 2 h. The reaction mixture was diluted to about 50 mL with $CH_2Cl_2$ and washed 3 times (25 mL) with saturated sodium bicarbonate solution and then 2 times with water. The volume of the solution was reduced to about 5 mL under vacuum and passed through 25 mL of silica in diethyl ether. The eluate was reduced to an off-white powder under vacuum. This yielded 820 mg (2.03 mmol) of the N-hexadecyliodoacetamide (71.8% yield). The 300 MHz $^1$H NMR spectra of the product was consistent with the expected structure.

Synthesis of N-Hexadecylacetamide-S-ACP

E. coli ACP prepared as above (10 mg in 2 mL of 50 mM Tris-Cl, pH 7.6) was treated at 37° C. with 50 mM DTT for 2 h. The solution was made to 10% trichloroacetic acid (TCA), held at 0°0 C. for 20 min and centrifuged to pellet. The resultant pellet was washed (2×2 mL) with 0.1M citrate, pH 4.2 and redissolved in 3 mL of 50 mM potassium phosphate buffer. The pH of the ACP solution was adjusted to 7.5 with 1M KOH and 3 mL of N-hexadecyliodoacetamide (3 mM in 2-propanol) was added. A slight precipitate of the N-hexadecyliodo-acetamide was redissolved by warming the reaction mix to 45° C. The mixture was held a 45° C. for 6 h. SDS-PAGE on 20% acrylamide PAGE gel showed approximately 80% conversion to an ACP species of intermediate mobility between the starting, reduced ACP and authentic palmitoyl-ACP. Excess N-hexadecyliodo acetamide was removed from the reaction mix by 4 extractions (3 mL) with $CH_2Cl_2$ with gentle mixing to avoid precipitation of the protein at the interface.

Coupling of N-Hexadecylacetamido-S-ACP to CNBr-activated Sepharose 4B

Cyanogen bromide-activated Sepharose 4B (Pharmacia, 2 g) was suspended in 1 mM HCl and extensively washed by filtration and resuspension in 1 mM HCl and finally one wash in 0.1M $NaHCO_3$, pH 8.3. The N-hexadecyl-acetamido-S-ACP prepared above was diluted with an equal volume of 0.2M $NaHCO_3$, pH 8.3. The filtered cyanogen bromide-activated Sepharose 4B (about 5 mL) was added to the N-hexadecylacetamide-S-ACP solution, the mixture was made to a volume of 10 mL with the 0.1M $NaHCO_3$, pH 8.3, and mixed by tumbling at room temperature for 6 h. Protein remaining in solution (Bradford assay) indicated approximately 85% binding. The gel suspension was collected by centrifugation, washed once with the 0.1M $NaHCO_3$, pH 8.3, and resuspended in 0.1M ethanolamine adjusted to pH 8.5 with HCl. The suspension was allowed to stand at 4° C. overnight and then washed by centrifugation and re-suspension in 12 mL of 0.1M acetate, pH 4.0, 0.5M in NaCl and then 0.1M $NaHCO_3$, pH 8.3, 0.5M in NaCl. The alkyl-ACP Sepharose 4B was packed into a 1×5.5 cm column and washed extensively with 20 mM bis-tris propane-Cl (BTP-Cl), pH 7.2, before use.

ACYL-ACP THIOESTERASE ASSAY

Acyl-ACP thioesterase was assayed as described by McKeon et al., (J. Biol. Chem. (1982) 257:12141–12147). Each of the radiolabeled acyl-ACP's were adjusted to concentrations ranging from 0.05 μM to 1.5 μM and a volume of 25 μL with a reaction buffer consisting of 1 mg/mL bovine serum albumin in 0.1M Tricine buffer at pH 8.2. Reactions were started with 5 μL of soybean seed extract containing acyl-ACP thioesterase activity and incubated for times varying from 12 sec to 5 min depending upon the activity of the fraction. Reactions were terminated by the addition of the 100 μL of a solution of 5% acetic acid in 2-propanol and extracted twice with 1 mL each of water saturated hexane. Five mL of ScintiVerse Bio HP (Fisher) scintillation fluid was added to the combined extracts and radioactivity in the released fatty acids was determined by scintillation counting.

For routine assays during acyl-ACP thioesterase purification [$^{14}$C]stearoyl-ACP at a concentration of 0.6 μM was used in the assay as described above.

PURIFICATION OF SOYBEAN ACYL-ACP THIOESTERASE

Developing soybean seeds (*Glycine max* cultivar Wye), ca. 20–25 days after flowering, were harvested and stored at −80° until use. One kg of the seeds were added while frozen to 2 L of a buffer consisting of 50 mM TRIS/HCl pH 8.0, 2 mM DTT and 0.2 mM EDTA in a Waring blendor and ground until thawed and homogenized. The homogenate was centrifuged at 14,000 xg for 20 min, decanted and the supernatant was centrifuged at 35,000 xg for 45 min. The resulting high speed supernatant was adjusted to 55% saturation with ammonium sulfate at 4° and protein was allowed to precipitate for 30 min before centrifugation at 14,000 xg for 15 min to remove precipitated proteins. The precipitated was dissolved in 50 mM BTP-HCl buffer, pH 7.2, 1 mM in 2-mercapto-ethanol and dialyzed overnight against 15 L of the same buffer at 5 mM. The dialyzed ammonium sulfate fraction was adjusted to a buffer concentration of 20 mM, a protein concentration of 5 mg/mL and Triton X-100 was added to a final concentration of 0.02%. One third of the resulting solution was applied to a 250 mL column of Blue sepharose contained in a radial flow column. The flow rate was approximately 75 mL/min and the column wash washed with the application buffer until the absorbance at 280 nm monitored at the column efflux returned to zero after application of the protein. Acyl-ACP thioesterase activity was eluted with 1M NaCl in the same buffer and the column was washed with an additional three column volumes of the salt containing buffer before re-equilibration with six column volumes of the starting buffer. This procedure was repeated twice more to bind and elute all of the acyl-ACP thioesterase activity present in the 55% ammonium sulfate fraction.

The combined Blue sepharose eluated were brought to 85% saturated in ammonium sulfate at 4°, allowed to precipitate for 30 min, then centrifuged to at 20,000 xg for 20 min. The resulting pellet was redissolved in 20 mM TRIS-HCl, pH 7.4, 0.2 mM in EDTA and 1 mM in DTT then dialyzed overnight against 4 L of the same buffer. The dialysate was centrifuged at 22,000 xg for 20 min then applied at a flow rate of 5 mL/min to Mono Q HR 16/10 anion exchange column (Pharmacia) equilibrated in the same buffer. After application of the protein, the column was washed with the same buffer until the absorbance at 280 nm monitored at the column efflux returned to near zero. The loaded column was re-equilibrated to pH 8.5 with 20 mM TRIS-HCl, and after the pH monitored at the column efflux was stable at that pH, elution was begun with the following program: NaCl concentration in the TRIS buffer system was increased linearly from 0 to 0.1M over 10 min, then held at 0.1M for 10 min. The NaCl concentration was then increased linearly from 0.1M to 0.3M over 80 min. The acyl-ACP thioesterase activity eluted broadly from an NaCl concentration of 0.165M to 0.275M. Active fractions were pooled, precipitated with ammonium sulfate as after Blue sepharose elution, redissolved in 20 mM BTP-HCl at pH 7.2 and dialyzed overnight against 20 L of the same buffer at 5 mM. After dialysis, the Mono Q fraction was adjusted to 20 mM BTP-HCl and 0.02% Triton X-100 before application to the alkyl-ACP affinity column. The column was loaded at 1 mL/min, then washed with the application buffer until the absorbance at 280 nm monitored at the column efflux returned to zero. The column was then washed with 0.1M NaCl in the same buffer until a protein peak was washed from the column and the column efflux 280 nm absorbance returned to zero before elution of the acyl-ACP thioesterase activity with 1M NaCl in the BTP-HCl buffer system.

The eluant from the alkyl-ACP column was made to 1M in ammonium sulfate and applied at flow rate of 0.5 mL/min to a Phenyl Superose HR 5/5 column (Pharmacia) which was equilibrated with 1M ammonium sulfate in 50 mM potassium phosphate buffer at pH 7.0. After sample application, the column was washed with equilibration buffer until the absorbance at 280 nm returned to zero and then eluted with a 20 mL gradient from 1M ammonium sulfate in the potassium phosphate buffer to the buffer alone.

Acyl-ACP thioesterase containing fractions from the Phenyl Superose column contained from 400 to 600 μg of protein and were enriched in specific activity of the acyl-ACP thioesterase by from 8,500 to 10,500 fold depending upon the preparation. Gel filtration chromatography of the Phenyl Superose purified acyl-ACP thioesterase on an Ultro-Pac TSK G200 SW (0.75×60 cm, Pharmacia) eluted with 0.1M potassium phosphate buffer at 1 mL/min gave one major protein peak which also corresponded with the acyl-ACP thioesterase activity. The molecular size estimation of that peak was approximately 75 kD. Analysis of the peptides present in the gel filtration purified acyl-ACP thioesterase showed three peptides of 39, 34 and 33 kD in size. The peptide at 39 kD was always least abundant and was not clearly visible in some preparations. Of the 34 and 33 kD peptides, the abundance of the 34 kD peptide slightly exceeds that of the 33. Further separation of these three peptides with retention of thioesterase activity has not been possible.

Antibody Precipitation of Soybean Seed Acyl-ACP Thioesterase

Acyl-ACP thioesterase purified through the Phenyl Superose step was denatured with DTT and SDS applied to a gradient polyacrylamide gel (9 to 15% acrylamide) and subjected to SDS electrophoresis. The developed gel was stained with a 9:1 mixture of 0.1% Coomassie blue in 50% methanol to 0.5% Serva blue in 50% methanol then partially destained with 3% glycerol in 20% methanol. The peptide doublet at 33 and 34 kD was cut from the gel, frozen in liquid nitrogen, then ground to a powder and suspended in 50 mM sodium phosphate buffer. The suspended gel with protein was sent for antibody production in New Zealand White rabbit by Hazelton Research Products Inc. Denver, Pa. Serum obtained after three injections of the combined 33 and 34 kD peptides identified those peptides in Western analysis, but also cross-reacted with the much less abundant peptide at 39 kD which was not included in the antigen preparations. The anti-33 and 34 kD serum was purified by immune affinity chromatography. Approximately one mg of acyl-ACP thioesterase purified through the Phenyl Superose step of the purification sequence described above was bound to DNBr activated sepharose (Pharmacia) according to the manufacturer's instructions. Five mL of the antiserum was equilibrated in 10 mM potassium phosphate buffer (pH 7.4) by gel filtration, mixed with the antigen bound to sepharose and allowed to bind overnight at 4°. The sepharose was poured into a small column and washed with 5 column volumes of the phosphate buffer then eluted with 0.1M glycine (pH 2.5). Fractions of 0.9 mL were collected in tubes containing 0.05 mL of 2M TRIS and 1 mg of bovine serum albumin. Fractions containing the anti-33 and 34 kD peptide immunoglobin were identified by using each fraction as the antibody in Western analysis. Active fractions were pooled and concentrated to approximately 50 µL by membrane concentration.

Soybean seed acyl-ACP thioesterase was purified through the Mono-Q anion exchange step described in the scheme above. Fold purification over the starting extract was about 60. Ten µL of this preparation was added to 2 µL of 0.1M TRIS/glycine buffer (pH 8.0) which contained from 0 to 2 µL of the purified antibody preparation. The solution was incubated for 45 min at room temperature, then 20 µL of Protein A-sepharose (Sigma) was added and the mixture was incubated an additional 30 min. The Protein A-sepharose was removed by centrifugation and 3 µL of the supernatant was taken for the standard acyl-ACP thioesterase assay. Pre-immune serum from the rabbit was diluted 1 to 10 in the incubation mix with the acyl-ACP thioesterase preparation, incubated and treated with Protein A-sepharose as above for a control. Net activity of the acyl-ACP thioesterase preparation after treatment with various dilutions of the antibody are shown below:

TABLE 2

| Dilution of antibody | Net pmol/µL/min |
| --- | --- |
| 1 to 1000 | 3.46 |
| 1 to 500 | 3.60 |
| 1 to 100 | 3.85 |
| 1 to 50 | 2.24 |
| 1 to 25 | 0.90 |
| 1 to 16.6 | 0.29 |
| 1 to 12.5 | 0.26 |
| 1 to 10 | 0.30 |
| 1 to 5 | 0 |
| Pre-immune 1 to 10 | 3.46 |
| No antibody | 4.07 |

The acyl-ACP thioesterase can thus be precipitated by the anti-33 and 34 kD antiserum, indicating that these two peptides are either all or part of the soybean seed thioesterase enzyme.

N-Terminal and Internal Amino Acid Sequence from the Acyl-ACP thioesterase

Acyl-ACP thioesterase purified through the Phenyl Superose step of the standard scheme was purified by reversed-phase chromatography to remove the small amount of the 39 kD peptide and a trace of lower molecular weight contaminant. One hundred µg of the preparation in 1 mL total volume was made to 0.1% trifluoroacetic acid (TFA) and loaded at 0.2 mL/min onto a Vydek diphenyl reversed phase column. The column was washed for 20 min with 0.1% TFA, then eluted by stepping to 25% acetonitrile in 0.1% TFA, washing for 8 min then eluting with a gradient from 25 to 70% acetonitrile in 0.1% TFA. The 33 and 34 kD peptides eluted together at 35.5% acetonitrile.

The combined peptides in the reverse phase purified fraction were used to determine the N-terminal amino acid sequence on an Applied Biosystems 470A Gas Phase Sequencer. PTH amino acids were analyzed on an Applied Biosystems 120 PTH amino Acid Analyzer. The N-terminal sequence was determined to be:

R-V-E-A-P-G-G-T-L-A-D-R-L (SEQ ID NO:5).

Other residues were present in most cycles, most notably the P in cycle 5 and the G in cycle 6.

Internal fragments of the combined peptides were also generated by CNBr cleavage. Acyl-ACP thioesterase purified through the Phenyl Superose step in the purification scheme (400 µg in 290 µL) was denatured by the addition of 24 µL of $^1$M TRIS at pH 8.0, 15 mg of DTT, 31 µL of 0.5M EDTA and solid guanidine-HCl to make the solution 6M in guanidine. The solution was incubated at room temperature for 2.5 h before the addition of 33 µL of 4-vinyl-pyridine and then incubated an addition 4 h. The solution was desalted by dilution to 2.5 mL and passage through a sephadex G-25 column which had been equilibrated in 2 mM TRIS, pH 8.0. The solution was lyophilized, redissolved in 400 µL of 70% TFA, placed in a sealable flask then evacuated and flushed with $N_2$. CNBr (2 mg in 2 µL of 70% TFA) was added and the flask was again evacuated and flushed with $N_2$. After incubation for 20 h in the dark at room temperature, the reaction mixture was diluted to 4 mL with water and again lyophilized. The residue was dissolved in water and approximately 200 µg (on the basis of the starting protein) was precipitated with 10% trichloroacetic acid (TCA). The resulting pellet was removed by centrifugation, then washed in sequence with acetone, 1% TCA and acetone again. The washed pellet was dissolved in 100 µL of 1% SDS with 7% glycerol and loaded onto a 20% crosslinked polyacrylamide gel for electrophoresis. The developed gel was electrophoretically blotted onto Immobilon membrane (Millipore), stained with 0.5% coomassie blue in 50% methanol and destained with 50% methanol. Three prominent bands of about 28 kD, 16 kD and 14 kD were cut from the Immobilon, and the N-terminal sequence of each was determined by gas phase sequencing as described above. With the exceptions of the 5th, 6th and 8th cycles, the sequence of the 28 kD fragment was identical to the N-terminal of the non-CNBr treated protein although other residues were present in all cycles. Nine cycles of sequence were obtained from the 16 kD band and 16 from the 14 kD band. The first nine cycles were identical for the two peptides, and the common sequence obtained for the fragments is as follows:

I-E-I-Y-K-Y-P-A-W-L-D-I-V-E-I (SEQ ID NO:6).

Cloning of Soybean Seed Acyl-ACP Thioesterase cDNA

Based on the N-terminal sequence from cycle 2 through 11, a set of 64 degenerate 29 nucleotide-long probes were designed for use as a hybridization probe:

(SEQ ID NO:7)
PROTEIN SEQUENCE: V E A P G G T L A D (SEQ ID NO:8)
DNA SEQUENCE: 5'- GTT GAA GCN CCA GGA GGN ACN TTT GCA GA
                      G   G       T   T       C G      T (SEQ ID NO:9)
PROBE: 5'-GTT GAA GCI CCA GGI GGI ACI TTT GCA GA
             G   G       T           C G       T

The design took into account the codon bias in representative soybean seed genes encoding Bowman-Birk protease inhibitor (Hammond et al., J. Biol. Chem. (1984) 259:9883–9890), glycinin subunit A-2B-1a (Utsumi et al., Agric. Biol. Chem. (1987) 51:3267–3273), lectin (1e-1) (Vodkin et al., Cell (1983) 34:1023–1031), and lipoxygenase-1 (Shibata et al., J. Biol. Chem. (1987) 262:10080–10085). Four deoxyinosines were used at selected positions of ambiguity.

A cDNA library was made as follows: Soybean embryos (ca. 50 mg fresh weight each) were removed from the pods and frozen in liquid nitrogen. The frozen embryos were ground to a fine powder in the presence of liquid nitrogen and then extracted by Polytron homogenization and fractionated to enrich for total RNA by the method of Chirgwin et al. (Biochemistry, (1979) 18:5294–5299). The nucleic acid fraction was enriched for polyA+ RNA by passing total RNA through an oligo-dT cellulose column and eluting the polyA+ RNA by salt as described by Goodman et al. (Meth. Enzymol. (1979) 68:75–90). cDNA was synthesized from the purified polyA+ RNA using cDNA Synthesis System (Bethesda Research Laboratory) and the manufacturer's instructions. The resultant double-stranded DNA was methylated by DNA methylase (Promega) prior to filling-in its ends with T4 DNA polymerase (Bethesda Research Laboratory) and blunt-end ligating to phosphorylated EcoRI linkers using T4 DNA ligase (Pharmacia). The double-stranded DNA was digested with EcoRI enzyme, separated from excess linkers by passing through a gel filtration column (Sepharose CL-4B), and ligated to lambda ZAP vector (Stratagene) as per manufacturer's instructions. Ligated DNA was packaged into phage using Gigapack packaging extract (Stratagene) according to manufacturer's instructions. The resultant cDNA library was amplified as per Stratagene's instructions and stored at −80° C.

Following the instructions in Lambda ZAP Cloning Kit Manual (Stratagene), the cDNA phage library was used to infect E. coli BB4 cells and plated to yield ca. 35,000 plaques per petri plate (150 mm diameter). Duplicate lifts of the plates were made onto nitrocellulose filters (Schleicher & Schuell). Duplicate lifts from five plates were prehybridized in 25 mL of Hybridization buffer consisting of 6X SSC (0.9M NaCl, 0.09M sodium citrate, pH 7.0), 5X Denhardt's [0.5 g Ficoll (Type 400, Pharmacia), 0.5 g polyvinylpyrrolidone, 0.5 g bovine serum albumin (Fraction V; Sigma)], 1 mM EDTA, 1% SDS, and 100 ug/mL denatured salmon sperm DNA (Sigma Chemical Co.) at 45° C. for 10 h. Fifty pmol of the hybridization probe (see above) were end-labeled in a 52.5 uL reaction mixture containing 50 mM Tris-Cl, pH 7.5, 10 mM $MgCl_2$, 0.1 mM spermidine-HCl (pH 7.0), 1 mM EDTA (pH 7.0), 5 mM DTT, 200 µCi (66.7 pmol) of gamma-labeled $AT^{32}P$ (New England Nuclear) and 25 units of T4 polynucleotide kinase (New England Biolabs). After incubation at 37° C. for 45 min, the reaction was terminated by heating at 68° C. for 10 min. Labeled probe was separated from unincorporated $AT^{32}P$ by passing the reaction through a Quick-Spin™ (G- 25 Sephadex®) column (Boehringer Mannheim Biochemicals). The purified labeled probe ($1.2 \times 10^7$ dpm/pmol) was added to the prehybridized filters, following their transfer to 10 mL of fresh Hybridization buffer. Following incubation of the filters in the presence of the probe for 48 h in a shaker at 48° C., the filters were washed in 200 mL of Wash buffer (6X SSC, 0.1% SDS) five times for 5 min each at room temperature, then at 48° C. for 5 min and finally at 62° C. for 5 min. The washed filters were air dried and subjected to autoradiography on Kodak XAR-2 film in the presence of intensifying screens (Lightening Plus, DuPont Cronex®) at −80° C. overnight. Size positively-hybridizing plaques were subjected to plaque purification as described in Sambrook et al. (Molecular Cloning, A Laboratory Manual, 2nd ed. (1989), Cold Spring Harbor Laboratory Press). None of the potential positives purified to completion and all were eventually dropped as false positives.

A second oligonucleotide probe was constructed based on the amino acid sequence derived from the CNBr fragments at 14 and 16 kD as follows:

(SEQ ID NO:10)
PROTEIN SEQUENCE I E I Y K Y P A W L D I E I (SEQ ID NO:11)
DNA SEQUENCE:5'-ATN GAA ATN TAC AAA TAC CCN GCN TGG CTN GAC ATN GAA ATN
                      G       T G T   T           T       T         G (SEQ ID NO:12)
PROBE: ATT GAA ATI TAT AAA TAT CCI GCI TGG TTI GAT ATI GAA AT
           G       G                               G

The design is based on the same codon bias assumptions as the N-terminal probe described above, with the additional simplification of eliminating the C at all G/C ambiguities. Probe radiolabeling was done as described for the N-terminal probe and hybridization of nitrocellulose lifts was done similarly, except that the hybridization temperature was lowered to 37° C. Screening of five plates with approximately 33,000 plaques each produced five positives which were then plaque purified. Of the five positives, four purified and isolated plaques could be taken corresponding to radioactive signals on the lifts in the second round of purification.

Following the Lambda ZAP Cloning Kit Instruction Manual (Stratagene), sequences of the pBluescript vector, including the cDNA inserts, from each of four purified phages were excised in the presence of a helper phase and the resultant phagemids were used to infect *E. coli* XL-1 Blue cells resulting in double-stranded plasmids, p22A, p22B, p25A and p25B. Purity of the clones were checked by colony hybridization and a single, positive colony from each was used for culture preparation.

DNA from the plasmids was made by the alkaline lysis miniprep procedure described in Sambrook et al. (Molecular Cloning, A Laboratory Manual, 2nd Ed. (1989) Cold Spring Harbor Laboratory Press). The alkali-denatured double-stranded DNA from p22B was sequenced using Sequenase" T7 DNA polymerase (US Biochemical Corp.) and the manufacturer's instructions. The sequence of the cDNA insert in plasmid p22 B is shown in SEQ ID NO:1.

EXAMPLE 2

EXPRESSION OF SOYBEAN SEED ACYL-ACP THIOESTERASE IN *E. COLI*

Construction of β-Galactosidase-Acyl-ACP Thioesterase Fusion Protein

Sequences which are inserted in pBluescript directionally correct and in-frame with the start methionine of the interrupted β-galactosidase gene borne on the plasmid are capable of being expressed as fusion proteins consisting of the N-terminal sixteen amino acids of β-galactosidase plus those encoded by the inserted sequence. Sequencing of p22B revealed that the cDNA insert of that plasmid was directionally correct but 1 base out of frame. Two μg of p22 B was digested for 2 h with 30 units of Bam HI. This cleaves once in the polylinker site of the Bluescript portion of the plasmid and once at a Bam HI site beginning at base 282 of the insert in p22. The complete digestion gave two fragments, one of 301 bases from the 5' end of the cDNA insert and a portion of the poly linker region of Bluescript, and a 4.2 kB fragment composed of Bluescript and the 3' 1320 bases of the cDNA insert. The 4.2 kB fragment was purified by electrophoretic separation on a 6% polyacrylamide gel run in TRIS/borate/EDTA buffer. The fragment was visualized by ethidium bromide staining, cut from the gel, eluted into TRIS/EDTA buffer overnight at 37° and precipitated by the addition of sodium acetate to 0.3M and ethanol to 50%. The two half-Bam HI sites on the purified fragment were re-ligated by incubation of 50 ng of the fragment in a 25 μL reaction with eight units of T4 DNA ligase overnight at 16° C. Competent *E. coli* XL-1 blue cells (Stratagene) were transformed with 30 ng of the ligated plasmid. Transformants were picked as ampicillin-resistant cells after overnight growth. Eight colonies were chosen and mini-preparations of plasmid DNA were made by the alkaline lysis procedure described above. Agarose gel electrophoresis of the uncut plasmids next to supercoiled weight standards showed that all eight plasmids were approximately 4.2 kB in size. The eight transformed cell lines containing plasmids designated p22Ba through 22Bh along with untransformed XL-1 blue cells and the transformed line carrying p22B were grown overnight in 5 mL of TB media with 0.2% glucose. The overnight cultures were diluted 1:1 into fresh TB+ glucose media which also contained 10 mM isopropyl thiogalactoside and growth was continued for 1.5 h at 37° C. Cells were harvested by centrifugation and re-suspended in 1 mL of 50 mM TRIS, pH 8.0. A subsample containing 10 μg protein was taken and added to 20 μL of SDS sample buffer for analysis by SDS-PAGE and western blotting. The remaining sample was made to 10 mM with DTT, 0.2 mM with PMSF and broken by probe sonication. Cell debris was removed by centrifugation and 5 μL of the extract was used in the standard acyl-ACP thioesterase assay using stearoyl-ACP as the substrate. The results are shown in Table 3.

TABLE 3

| Extract | Net reaction (pmol/μL/min) |
| --- | --- |
| XL-1 blue | 0.42 |
| p22B | 0.58 |
| p22Ba | 2.17 |
| p22Bb | 2.05 |
| p22Bc | 2.25 |
| p22Bd | 2.17 |
| p22Be | 2.11 |
| p22Bf | 2.25 |
| p22Bg | 2.84 |
| p22Bh | 1.71 |

While p22 B does not have activity significantly greater than the endogenous *E. coli* activity, thioesterase activity was greatly increased by the combination of removing the transit peptide and placing the construction in-frame relative to the fusion protein start methionine. Western analysis of the proteins produced by each of the cell lines also showed a single, antibody-positive signal of about 42 kD in size produced by each of the in-frame plasmids, but not signal produced by plasmid p22B.

Plasmid p22Ba was chosen for more detailed analysis using both palmitoyl and oleoyl-ACP as substrates. Cells containing p22B were used as the controls indicative of the endogenous *E. coli* thioesterase. When palmitoyl-ACP was used as substrate, p22B cell extract showed a low but measurable reaction rate while that of the p22Ba-containing cells was ten fold higher. When oleoyl-ACP was used as substrate, the rate of acyl-ACP hydrolysis by extract form the p22Ba-containing cells was 96 fold greater than that of the controls.

EXAMPLE 3

USE OF SOYBEAN SEED ACYL-ACP THIOESTERASE SEQUENCE IN PLASMID AS A RESTRICTION FRAGMENT LENGTH POLYMORPHISM (RFLP) MARKER

The cDNA insert from plasmid p22B was removed from the Bluescript vector by digestion with restriction enzyme EcoRI in standard conditions as described in Sambrook et al. (Molecular Cloning, A Laboratory Manual, 2nd ed. (1989) Cold Spring Harbor Laboratory Press) and labeled with $^{32}$P using a Random Priming Kit from Bethesda Research Laboratories under conditions recommended by the manufacturer. The resulting radioactive probe was used to probe a Southern blot (Sambrook et al., Molecular Cloning, A Laboratory Manual, 2nd ed. (1989) Cold Spring Harbor Laboratory Press) containing genomic DNA from soybean (*Glycine max* (cultivar Bonus) and *Glycine soja* (PI81762)), digested with one of several restriction enzymes. After hybridization and washes under standard conditions (Sambrook et al., Molecular Cloning, A Laboratory Manual, 2nd ed. (1989) Cold Spring Harbor Laboratory Press), autoradiograms were obtained and different patterns of hybridization (polymorphisms) were identified in digests performed with restriction enzymes Pst 1 and Eco RI. The same probe was then used to map the polymorphic p22B loci on the soybean genome, essentially as described by Helentjaris et al. (Theor. Appl. Genet. (1986) 72:761–769). Plasmid pDS1 probe was applied, as described above, to Southern blots of EcoRI, PstI, EcoRV, BamHI, or HindIII digested genomic DNAs isolated from 68 F2 progeny plants resulting from a G. max Bonus×G. soja PI81762 cross. The bands on the autoradiograms were interpreted as resulting from the inheritance of either paternal (Bonus) or maternal (PI81762) pattern, or both (a heterozygote). The resulting data were subjected to genetic analysis using the computer program Mapmaker (Lander et al., Genomics (1987) 1: 174–191). In conjunction with previously obtained data for 436 anonymous RFLP markers in soybean (S. Tingey et al., J. Cell. Biochem., Supplement 14E (1990) p. 291, abstract R153), we were able to position one genetic locus corresponding to the p22B probe on the soybean genetic map. This information will be useful in breeding soybean lines with altered saturate levels.

EXAMPLE 4

USE OF SOYBEAN SEED ACYL-ACP THIOESTERASE SEQUENCE IN PLASMID P22B AS A PROBE FOR ADDITIONAL SOYBEAN ACYL-ACP THIOESTERASE GENES

The cDNA insert in plasmid p22B was removed by digestion with EcoRI and purified by electrophoretic separation on 6% polyacrylamide. The 1.6 kB fragment was localized by ethidium bromide staining, eluted from the gel and precipitated from 0.3M sodium acetate with 50% ethanol. Thirty ng of the resulting DNA fragment was used as the template in a random primer labeling reaction using a labeling kit from Bethesda Research Laboratories. The early development soybean seed cDNA library described in Example 1 was re-plated at a plaque density of 35,000 per plate and duplicate nitrocellulose lifts from four plates were screened. The pre-hybridization and hybridization buffer was that described in Example 1, but the probe annealing conditions were 50° for 40 h. The filter lifts were washed 3 times at room temperature with 0.6 x SSC containing 0.1% SDS, then once at 50° C. for 5 min in the same solution. Two additional washes were given for 5 min each at 50° C. in 0.2 x SSC, 0.1% SDS followed by a 1 min rinse under the same conditions.

After autoradiography for 20 h, ten hybridizing plaques were identified. These were plaque purified and excised into Bluescript plasmids as described in Example 1. To check for the similarity of the cDNA inserts in these plasmids to the sequence of soybean seed acyl-ACP thioesterase copy 1 shown in SEQ ID NO:1, a 30 base oligonucleotide was prepared for use as the extension primer in dideoxy sequencing reactions. The primer corresponded to bases 1028 to 1058 in the sequence of SEQ ID NO:13.

The placement of the primer oligonucleotide on cDNA's similar to that found in p22B should allow sequencing the 3' 100 bases of the open reading frame and 100 to 170 bases of the 3' untranslated region. Bluescript plasmids purified from six of the ten positively hybridizing clones described above were sequenced. Of these, one did not give a sequencing reaction with the primer. Sequencing from the universal and T3 primers of the Bluescript plasmid revealed that this clone was a partial cDNA, identical to the insert in p22B, but terminating 3' to the primer region. The sequences of the remaining five clones used as templates showed two classes of sequence, one clone identical through the region sequenced to the p22B and four examples of a second acyl-ACP thioesterase gene with a single base change in the portion of the open reading frame which was sequenced (at base 1094 of SEQ ID NO:1, C is changed to T) and decreased homology in the 3' non-coding region.

Nucleotide 1 of SEQ ID NO:1 is the first nucleotide of the EcoRI cut site reading from 5' to 3' on the cDNA insert and nucleotide 1602 is the last nucleotide of the cDNA insert in the EcoRI cut site of plasmid p22B which encodes copy 1 of the soybean seed acyl-ACP thioesterase. Nucleotides 106 to 108 are the putative translation initiation codon, nucleotides 271 to 273 are the codon for the N-terminal of the purified enzyme, nucleotides 1207 to 1209 are the termination codon, nucleotides 1 to 5 are the 5' untranslated sequence and nucleotides 1210 to 1602 are the 3' untranslated nucleotides.

Digestion of two of the plasmids (p4A and p4C) with EcoRI followed by analysis on agarose gel electrophoresis showed cDNA inserts of 1.0 and 1.4 kB respectively. Dideoxy sequencing of both plasmids showed them to be identical and the insert in p4C to be a full length clone. By the very high degree of homology between the open reading frames in p4C and p22B, p4C can reasonably be expected to encode a second acyl-ACP thioesterase. The base and amino acid sequences of soybean seed acyl-ACP thioesterase (copy 2) are shown in SEQ ID NO:3.

Nucleotide 1 of SEQ ID NO:3 is the first nucleotide of the EcoRI cut site reading from 5' to 3' on the cDNA insert and nucleotide 1476 is the last nucleotide of the cDNA insert in the EcoRI cut site of plasmid p4C which encodes copy 2 of the soybean seed acyl-ACP thioesterase. The putative initiation codon is nucleotides 117 to 119, the N-terminal of the mature protein is nucleotides 282 to 284, and the termination codon is nucleotides 1218 to 1220.

EXAMPLE 5 p22B AS A PROBE FOR ACYL-ACP THIOESTERASE GENES FROM BRASSICA NAPUS

The $^{32}$P-labeled probe produced by random primed labeling using the EcoRI fragment from p22B as described in EXAMPLE 4 was used to screen a genomic library made from Brassic napus cultivar Bridger DNA (Clontech commercial library). The library was plated on two plates at a density of approximately 60,000 plaques per plate and duplicate nitrocellulose lifts were taken for hybridization. The prehybridization and hybridization buffer was that described in Example 1 with annealing of the probe for 55 h at 42° C. The filter lifts were washed twice at room temperature with 0.6 x SSC containing 0.1% SDS followed by two 5 min washed and one 1 min wash in the same solution and all at 52° C.

Hybridizing plaques were identified by autoradiography for 18 h at −70° C. Of three positive signals present in the duplicate plates, two were chosen for plaque purification by removal from the plate, dilution and re-screening under the above described conditions. Single plaques from the two independent clones (designated pCAN11 and pCAN21) were chosen, cored to remove them from the plate, diluted and re-plated at low titer for amplification. Ten plaques from each of the clonal lines were selected, homogenized in buffer and used to inoculate a 0.5 mL culture of E. coli strain MN538 at a cell density of 0.5 OD$_{600}$. The inoculum was used to start a 100 mL culture in LB media and was grown to cell lysis. Phage DNA was purified from the culture as described in Sambrook et al. (Molecular Cloning, A Laboratory Manual, 2nd ed. (1989) Cold Spring Harbor Laboratory Press). DNA from the two clones was digested with the following combinations of restriction endonucleases: Sal I alone, Sal I+EcoRI, Sal I+Xba I, Sal I+NotI, and Sal I+Bam HI. The digests were subjected to electrophoresis on 1% agarose for blotting to Hybond-N (Amersham). Southern analysis after hybridization to the radiolabeled, random-primed probe from p22B as described above revealed that all hybridizing sequence from pCAN11 resided on a 3 kB Sal 1/Xba I fragment and that all hybridizing sequence from pCAN21 resided on a 6 kB Sal I/EcoRI fragment. These two fragments were again generated by digestion from the corresponding clone, purified from the other fragments by electrophoresis on 1% agarose, excised from the gel after ethidium bromide staining and removed from the agarose by treatment with Gelase (Epicentre Technologies), phenol extraction and ethanol precipitation of the aqueous phase. The fragments were ligated into the plasmid Bluescript SK+ (Stratagene) which had been double digested with the corresponding restriction endonucleases and used to transform competent E. coli cells. Both the ligation and transformation procedures were as described in Example 2 above. Three positives from pCAN21 and 5 positives from pCAN11 were found and confirmed by purification of plasmid DNA and digestion with the endonucleases used to generate the ligated inserts.

The shorter, 3 kB clone was chosen for sequencing by the dideoxy method as described in Example 1, above using the double-stranded Bluescript plasmid as the template. The clone was partially sequenced from the genomic insert in the M13 universal primer on pBluescript and two primers made corresponding to segments of p22B. That sequence is shown in SEQ ID NO:20. Sequence alignment with p22B (Deveraux et al. (1987) Sequence Analysis Package of the Genetics Computer Group, University of Wisconsin Biotechnology Center) showed a sequence identity of 73.6% after the insertion of eight gaps. The sections of alignment span 1170 bases of the pCAN11 insert and correspond approximately to bases 424 through 1027 in SEQ ID NO:1. Five of the eight pCAN11 sequences which do not align with p22 B appear to be introns, the remaining three gaps maybe introns or the combination of intron with coding regions which are less homologous with p22B. Assuming reasonable intron splicing, the resulting open reading frame encodes 168 amino acids of the putative thioesterase. Of these residues, 132 are identical to the soybean seed acyl-ACP thioesterase and fifteen residues present in the soybean protein are not accounted for in the gene from Brassica. Clone pCAN11 thus encodes a large portion of the Brassica acyl-ACP thioesterase.

EXAMPLE 6 p22B AS A PROBE FOR ACYL-ACP THIOESTERASE GENES FROM *CUPHEA LANCEOLATA* AND *CHUPEA VISCOSISSIMA*

Genomic clones of acyl-ACP thioesterases from *Cuphea viscosissima* and *Cuphea lanceolata* were obtained using a polymerase chain reaction (PCR) strategy using initiation primers based segments of the sequence of p22B. Three segments were chosen from the deduced amino acid sequence as amino acid sequences encoded by relatively non-degenerate DNA codons. These segments were synthesized to include all probable DNA sequences encoding the amino acid sequence. The sequences synthesized and their approximate corresponding bases in SEQ ID NO:1 are shown below. Positions at which all combinations of multiple bases were synthesized are denoted as combinations of bases inside parenthesis.

TC-58 5'-TA(T/C)AA(G/A)GA(GA)AA(GA)TT(T/C-3' (SEQ ID NO:14—corresponding to bases 343 through 357 of SEQ ID NO:1)

TC-59 5'-AA(A/G)TGGGT(A/T/G/C)ATGATGAA(T/C)CAA-3'] (SEQ ID NO:15—corresponding to bases 676 through 696 of SEQ ID NO:1)

TC-60 5' (C/T)TG(A/G)TTCATCAT(A/T/G/C)ACCCA(T/C)TT-3' (SEQ ID NO:16—corresponding to the complementary strand of TC-59)

TC-61 3'-CT(T/C)CT(C/A)TT(T/C(GT(A/G(CT(T/C)FT(G/A)GT(T/C)GT(C/T)-5' (SEQ ID NO:17—corresponding to complementary strand of bases 1125 through 1101 of SEQ ID NO:1).

Four PCR reactions were run using buffers, deoxynucleotides, TAQ polymerase and reaction conditions from a GENEAMP kit (Perkin-Elmer/Cetus), with 200 ng of genomic DNA from either C. lanceolata or C. viscosissima as template and either TC-58 and TC-60 or TC-59 and TC-61 as the sense and antisense primers. The degenerate primers were used at a final concentration of 1 mM. The temperature cycling reactions were carried out in a Perkin-Elmer/Cetus Thermocycler with the temperature at the annealing cycle set to 37° C. The extension and denaturation steps were 72° C. and 92° C. respectively and 30 cycles were preformed.

No products were formed with the TC-59/TC-61 primer set. A product of about 0.7 kB in size was formed with the TC-58/TC-60 primer set using genomic DNA from either species as template. The 0.7 kB fragment from both species was purified from several minor products also present in the initial PCR reaction and used as the template for re-amplification using the same conditions as in the initial reaction. Both products amplified and were again gel purified for blunt-end cloning into Eco RV-cut and phosphatase-treated Bluescript SK. One hundred ng of both fragments were used in a 10 µL ligation reaction at 12° C. overnight. One µL of the ligation mix was used to transform 100 µL of competent E. coli cells. Transformants were recovered by plating on plates containing amphicillin (150 µg/mL) to which was also added 50 µL of 5-bromo-4-chloro-3-indolyl-β-D-galactopyrannoside (X-gal) (20 µg/mL) and 10 µL of 100 mM IPTG. Six white colonies were recovered from the C. lanceolata transformation and seven from the C. viscosissima transformation. Plasmid DNA was prepared from each of the thirteen cell lines and digested with restriction endonucleases to excise the cloned insert from the Bluescript plasmid. One insert of the expected size was obtained from both species and double stranded plasmid was prepared from the each of the two cell lines for sequencing.

An 865 base pair insert was sequenced from C. viscosissima (SEQ ID NO:22) and an 852 base pair insert was sequenced from C. lanceolata (SEQ ID NO:21). Sequence alignment (Deveraux et al., (1987) Sequence Analysis Package of the Genetics Computer Group, University of Wisconsin Biotechnology Center) shows that the two sequences are 96.6% identical to one another. Similar alignment of the sequence from C. viscosissima with that of p22B (SEQ ID NO:1) shows an overall identity of 79.9% with the insertion of three gaps. The gaps appear to be introns and sequence ends are in agreement with the sequences of p22B which were used to design the PCR primers. Removal of the introns and translation of the resulting open reading frame gives two amino acid sequences which are 93% identical to the sequence derived from the corresponding base sequence of p22B. The two clones are thus partial copies of the genomic *C. viscosissima* and *C. lanceolata* acyl-ACP thioesterases.

EXAMPLE 7

CONSTRUCTION OF VECTORS FOR TRANSFORMATION OF PLANTS FOR ALTERED EXPRESSION OF ACYL-ACP THIOESTERASE

Sense and antisense expression constructions using the constitutive 35S promoter The starting vectors for the 35S constructions were p22B carrying the soybean seed acyl-ACP thioesterase gene and pK35K. pK35K was in turn derived from pKNK (WO91/09957). pKNK is a pBR322-based vector which contains a neomycin phosphotransferase II (NptII) promoter fragment, a nopaline synthase (NOS) promoter fragment, the coding region of NptII and the polyadenylation region from the NOS gene. A map of this plasmid is shown by Lin et al. (Plant Physiol. (1987) 84: 856–861). The 320 bp ClaI-BglII fragment in pKNK that contains the NptII promoter was obtained as a HindIII-BglII fragment from the NptII gene of the transposon Tn5 described by Beck et al. (Gene 1982) 19: 372–336). The HindIII site was converted to a ClaI site by linker addition. The NptII promoter fragment is followed by a 296 bp Sau3A-PstI NOS promoter (NOS/P) fragment corresponding to nucleotides −263 to +33, with respect to the transcription start site, of the NOS gene described by Depicker et al. (J. Appl. Gent. (1982) 1: 561–574). The PstI site at the 3' end was created at the translation initiation codon of the NOS gene. The NOS/P is followed by a 998 bp HindIII-BamHI sequence containing the NptII coding region obtained from the transposon Tn5 (Beck et al., (1982) Gene 19: 327–336) by the creation of HinkIII and BamHI sites at nucleotides 1540 and 2518, respectively. The NptII coding region is then followed by a 702 bp BamHI-ClaI fragment containing the 3' end of the nopaline synthase gene including nucleotides 848 to 1550 (Depicker et al., J. Appl. Genet. (1982) 1: 561–574). The remainder of pKNK consists of pBR322 sequences from 29 to 4361.

pKNK was converted to pK35K by removing the NptII and NOS promoters and replacing them with a CaMV 35S promoter. The EcoRI-HindIII 35S promoter fragment is the same as that contained in pUC35K (WO91/09957). The 35S promoter fragment was prepared as follows, and as described in Odell et al. (Nature (1985) 313: 810–813) except that the 3' end of the fragment includes CaMV sequences to +21 with respect to the transcription start site. A 1.15 kb BglII segment of the CaMV genome containing the region between −941 and +208 relative to the 35S transcription start site was cloned in the BamHI site of the plasmid pUC13. This plasmid was linearized at the SalI site in the polylinker located 3' to the CaMV fragment and the 3' end of the fragment was shortened by digestion with nuclease Bal31. Following the addition of HindIII linkers, the plasmid DNA was re-circularized. From nucleotide sequence analysis of the isolated clones, a 3' deletion fragment was selected with the HindIII linker positioned at +31. To create pK35K this 35S promoter fragment was isolated as an EcoRI-HindIII fragment, the EcoRI site coming from the polylinker of pUC13, and ligated to pKNK that had been digested with EcoRI and HindIII, the EcoRI site lying 5' to the ClaI site in pBR322.

pK35K was digested with BamHI and the cut ends were blunted using the Klenow fragment of DNA polymerase. Digestion with HinDIII, then removed the NptII coding region leaving pK35K linearized with a half HinDIII site at the 3' end of the 35S promoter sequence and a blunt end 5' to the NOS 3' region. Digestion of p22B with the combination of HinDIII and EcoRV released a fragment which begins twelve bases 5' to the start methionine of the soybean seed acyl-ACP thioesterase precursor protein and ends in the Bluescript vector just 3' to the 3' non-coding region of p22B. Gel purification of both the p22B-derived fragment and the modified pK35K fragment as described in Example 2 followed by ligation of the fragments with T4 DNA ligase gave pKTE9 which contains the coding sequence for soybean seed acyl-ACP thioesterase linked to the 35S promoter in a manner expected to produce a functional enzyme in an appropriate cell.

To produce an expression vector for production of antisense message from p22B, pK35K was digested with the combination of BamHI and HinDIII to remove the existing coding sequence for NptII and the ends of the remaining, linearized plasmid were blunted using the Klenow fragment of DNA polymerase. Two XmnI sites exist in p22B (at the 5' end coincident with the EcoRI used for cloning into pBluescript and spanning bases 1662 through 1672 at the 3' end of SEQ ID NO:1) so that digestion with XmnI removes the entire sequence of p22B including the 5' and 3' non-coding regions of the cDNA and leaves blunt ends. Gel purification of the desired fragments as described above followed by blunt end ligation and recovery of transformants gave both the sense and antisense orientations of p22B 3' to the 35S promoter. Orientation of the p22B insert in pK35L was determined by restriction mapping using the combination of restriction endonucleases EcoRI and BamHI. The combined digestion released a 1101 base pair fragment (950 bases from the pK35K plasmid and 116 bases from the XmnI insert from p22B) in the case of sense orientation of p22B with respect to the promoter and a 2365 base pair fragment in the case of antisense orientation (950 bases from pK35K and 1415 bases from the XmnI fragment of p22B). The antisense orientation construction (pKTER) is suitable for use in antisense constructs because it contains all of the 5' and 3' noncoding regions.

The soybean somatic embryo transformation described below requires the use of hygromycin as the selectable marker for transformation. To introduce this selectable marker into the vector, a second plasmid pML18 was constructed by the introduction of a DNA segment containing the 35S promoter from pK35K 5' to the hygromycin phosphotransferase gene from *E. coli* (Gritz et al. Gene (1983) 25:179) and 3' to the NOS 3' end. This segment was ligated into the SalI site of the plasmid pGEM9Z (Promega). To introduce the 35S:acyl-ACP thioesterase:NOS construction into pML18, pKTE9 was cut with AatI and ClaI and blunted with the Klenow fragment of DNA polymerase. AatI cuts pKTE9 just 5' to the 35S promoter and ClaI just 3' to the NOS 3' end. XbaI linkers were ligated to the blunt ended fragment, the fragment was purified by gel electrophoresis and ligated into the cut XbaI site of pML18. After transformation and recovery of clones, plasmid DNA was purified from several clones and the construct was restriction-mapped to determine the relative orientation of the two 35S:coding region units. A clone was selected which had the following orientation: In the poly restriction site of pGEM9Z, and oriented 3' to the f1 origin of replication; at the XbaI site is the 35S promoter followed by the coding region of the acyl-ACP thioesterase gene described above, followed by the NOS 3' end. Beginning at a second XbaI site is the second 35S promoter followed by the hygromycin phosphotransferase gene and the second NOS 3' end. The vector was given the name, pKR12.

A vector with hygromycin selection and antisense expression of the acyl-ACP thioesterase message was obtained by a similar strategy. To obtain compatible ends on the acyl-ACP thioesterase transcription unit in pKTER, the plasmid was digested with EcoRI and ClaI which released the 35S promoter, p22B derived sequence and NOS 3' end as a unit. The EcoRI and ClaI sites in the cloning region of pBluescript were cut and the purified EcoRI ClaI fragment from pKTER was ligated into pBluescript. A clone was isolated from transformed E. coli cells. This clone was cut at the XbaI site which is in the cloning region of pBluescript to create one XbaI end. The SalI site at the other end of the insert in pBluescript was digested, blunted and XbaI linkers were ligated to it to produce the second end. The resulting fragment was purified by gel electrophoresis and ligated into pML18 which had been digested by XbaI as above. A single clone was isolated from the transformation. This construction, pKR13, was determined by restriction mapping to have the same order of the two transcriptions units as described for pKR12.

Vectors for transformation of the acyl-ACP thioesterase gene under control of the 35S promoter into plant using Agrobacterium tumefaciens were produced by constructing a binary Ti plasmid vector system (Brevan, Nucl. Acids Res. (1984) 12:8711–8720). The vector (pZA199) is based on a vector which contains: (1) the chimeric gene nopaline synthase/neomycin phosphotrasferase as a selectable marker for transformed plant cells (Brevan et al., Nature (1984) 304: 184–186), (2) the left and right borders of the T-DNA of the Ti plasmid (Brevan et al., Nucl. Acids Res. (1984) 12:8711–8720), (3) the E. coli lacZ α-complementing segment (Vieria et al., Gene (1982) 19:259–267) with unique restriction endonuclease sites for EcoRI, KpnI, BamHI, HinDII, and SalI, (4) the bacterial replication origin from the Pseudomonas plasmid pVS1 (Itoh et al., Plasmid (1984) 11:206–220), and (5) the bacterial neomycin phosphotransferase gene from Tn5 (Berg et al., Proc. Natl. Acad. Sci. U.S.A. (1975) 72:3628–3632) as a selectable marker for transformed A. tumefaciens. The nopaline synthase promoter in the plant selectable marker was replaced by the 35S promoter by a standard restriction endonuclease digestion and ligation strategy. The 35S promoter is required for efficient Brassica napus transformation as described below.

For construction of the antisense expression vector, pZS199 was digested with EcoRI and SalI. pKTER was also digested with EcoRI and SalI to release the 35S:antisense acyl-ACP synthase:NOS transcriptional unit which was isolated by gel electrophoresis. The EcoRI/SalI fragment was ligated into the cut pZX199 and used to transform E. coli competent cells. Isolation of a clone and purification of the plasmid DNA gave the binary vector pZKR13.

The sense 35S construction was assembled by removing the acyl-ACP thioesterase coding region and a portion of the 3' untranslated region from p22B by digestion with HinKII and SspI. SspI cuts after base 1351 in SEQ ID NO:1. The HinII site was blunted, the fragment isolated by gel electrophoresis, and ligated into the HindII/BamHI and blunted version of pK35K described above. Clones resulting from the transformation of E. coli were restriction-mapped by cutting with BamHI and EcoRI. The sense-oriented insert gives a unique 1101 base fragment which is indicative of the sense orientation. The resulting plasmid (pKTE10) was cut at the EcoRI and SalI sites described in pK35K above and cloned into pBluescript cut with the same restriction endonucleases to give pBTE4.

Cloning into the high copy number plasmid pBTE4 allowed isolation of plasmid DNA which was digested with SalI and EcoRI. The resulting fragment containing the transcriptional unit 35S:acyl-ACP thioesterase:NOS was the ligated into pZS199 which had been similarly digested to give the desired sense expression vector pKR12.

For cloning the thioesterase sequence into existing expression vectors containing seed specific promoters, an NcoI site was engineered at the start methionine of p22B. For this purpose two PCR primers were synthesized:

KR40    5'-AAAAATCTAGAAGCTTTCGTGCCATG-GCTTGGACC-3') SEQ ID NO:18) corresponding approximately to bases 83 through 117 in SEQ ID NO:1. This created an XbaI site (substitutions at 89 and 91) and an NcoI site (substitution at 105).

KR41 5'-AGCGTACCGGGATCCGCCTCTA-3' (SEQ ID NO:19) corresponding approximately to the complementary strand of bases 274 through 296 in SEQ ID NO:1.

The polymerase chain reaction run with these two primers and p22B as the template amplified a 213 base pair fragment which contained the restriction endonuclease cleavage sites described in KR40 as well as an existing BamHI site in p22B (bases 282 through 287 in SEQ ID NO:1).

Most of the 3' untranslated region of p22B was removed by digestion with SspI and HinCII followed by re-ligation of the blunt ends to give pBTE8. Both the PCR amplified fragment and pBTE8 were digested with XbaI and BamHI. The remaining, linearized pBTE8 derived fragment was purified by gel electrophoresis and the two fragments were ligated to give the restriction site modified acyl-ACP thioesterase pPTE1.

The 5' and 3' regulatory sequences from the phaseolin gene of Phaseolus vulgaria described by Doyle et al. (J. Biol. Chem. (1986) 261:9228–9238) and containing the unique restriction endonuclease sites NcoI, SmaI, KpnI and XbaI between the 5' and 3' regulatory sequences were placed into the HinDII site in the cloning region of a pUC18 plasmid (BRL) to give the plasmid pCW108.

The NcoI to KpnI fragment cleaved from pPTE1 and purified by gel ectrophoresis, was ligated into pCW108 after digestion with the same two enzymes to give plasmid pPHTE1. Removal of the entire phaseolin 5':acyl-ACP thioesterase:phaseolin 3' transcriptional unit by digestion with HinDIII, gel purification of the fragment and ligation into HinDIII cut pBluescript gave pPHTE2. Cleavage of pPHTE2 at the EcoRI and SalI sites in the cloning region of the original pBluescript plasmid released the desired transcriptional unit with the EcoRI and SalI sites required for cloning into the Binary vector pZS199 as described above to give pZPHTE1.

The promoter region for the 2S2 albumin protein from Arabadopsis thaliana was obtained as 1250 base pairs 5' to the NcoI site which is coincident with the start ATG as described by Krebbers et al. (Plant Physiol. (1988) 87:859–866) along with the 750 base pair coding region ahead of a 1000 base pair 3' regulatory sequence from the octapine synthase (OCS) gene of Agrobacterium (DeGreve et al., J. Mol. Appl. Genet. (1982) 1:499–511) all contained in a pUC19 cloning vector (BRL). The 2S albumin coding sequence was removed from the vector by digestion with NcoI and XbaI which cleaves at the start ATG and just 3' to the 2S albumin stop codon in the OCS 3' regulatory sequence. The acyl-ACP thioesterase coding sequence from pTE1 was removed from the remainder of the plasmid by digestion with NcoI and XbaI and purified by gel electrophoresis. Ligation of the two fragments gave pSTE1.

A unique EcoRI site at the 5' end of the 2S2 promoter sequence and a HinDII site 3' to the OCS 3' sequence were digested to release the 2S2:acyl-ACP thioesterase:OCS transcriptional unit. The fragment was purified and ligated into the cut EcoRI and HinDIII sites described in pZS199 above to give the binary vector pZATE1.

EXAMPLE 8

TRANSFORMATION OF SOMATIC SOYBEAN EMBRYO CULTURES

Culture of Embryogenic Suspensions

Soybean embryogenic suspension cultures were maintained in 35 mL liquid media (SB55 or SBP6 described below) on a rotary shaker, 150 rpm, at 28° C. with mixed flourescent and incandescent lights on a 16:8 h day/night schedule. Cultures were subcultured every four weeks by inoculating approximately 35 mg of tissue into 35 mL of liquid medium.

Transformation

Soybean embryogenic suspension cultures were transformed by the method of particle gun bombardment (see Kline et al. Nature (1987) (London) 327:70). A DuPont Biolistic® PDS1000/HE instrument (helium retrofit) was used for these transformations.

DNA/Particle Preparation

To 50 µL of a 60 mg/mL 1 µm gold particle suspension was added (in order): 5 µL DNA (1 µg/µL), 20 µL spermidine (0.1M), and 50 µL $CaCl_2$ (2.5m). The particle preparation was agitated for three min, spun in a microfuge for 10 sec and the supernatant removed. The DNA-coated particles were then washed once in 400 uL 70% ethanol and resuspended in 40 µL of anhydrous ethanol. The DNA/particle suspension was sonicated three times for 1 sec each. Five µL of the DNA-coated gold particles were then loaded on each macro carrier disk.

Bombardment

Approximately 300–400 mg of a four-week-old suspension culture was placed in an empty 60×15 mm petri dish and the residual liquid removed from the tissue with a pipette. For each transformation experiment, approximately 5–10 plates of tissue were bombarded. Membrane rupture pressure was set at 1000 psi and the chamber was evacuated to a vacuum of 71 cm mercury. The tissue was placed approximately 8.9 cm away from the retaining screen and bombarded three times. Following bombardment, the tissue was placed back into liquid and cultured as described above.

Eleven days after bombardment, the liquid media was exchanged with fresh SB55 containing 50 mg/mL hydromycin. The selective media was refreshed weekly. Seven weeks after bombardment, green, transformed tissue was observed growing from untransformed, necrotic embryogenic clusters. Isolated green tissue was removed and inoculated into individual flasks to generate new, clonally propagated, transformed embryogenic suspension cultures. Thus, each new line was treated as independent transformation event. These suspensions could then be maintained as suspensions of embryos clustered in an immature developmental stage through subculture or regenerated into whole plants by maturation and germination of individual somatic embryos.

Maturation and Germination

Transformed embryogenic clusters were removed from liquid culture and placed on a solid agar media (SB103) containing no hormones or antibiotics. Embryos were cultured for eight weeks at 26° C. with mixed flourescent and incandescent lights on a 16:8 h day/night schedule. During this period, individual embryos were removed from the clusters and analyzed at various stages of embryo development.

| Media: SB55 and SBP6 Stock Solutions (grams per liter): | |
|---|---|
| MS Sulfate 100× Stock | |
| $MgSO_4\ 7H_2O$ | 37.0 |
| $MnSO_4\ H_2O$ | 1.69 |
| $ZnSO_4\ 7H_2O$ | 0.86 |
| $CuSO_4\ 5H_2O$ | 0.0025 |
| MS Halides 100× Stock | |
| $CaCl_2\ 2H_2O$ | 44.0 |
| KI | 0.083 |
| $CloCl_2\ 6H_2O$ | 0.00125 |
| $KH_2PO_4$ | 17.0 |
| $H_3BO_3$ | 0.62 |
| $Na_2MoO_4\ 2H_2O$ | 0.025 |
| MS FeEDTA 100× Stock | |
| $Na_2EDTA$ | 3.724 |
| $FeSO_4\ 7H_2O$ | 2.784 |
| B5 Vitamin Stock | |
| 10 g m-inositol | |
| 100 mg nicotinic acid | |
| 100 mg pyridoxine HCl | |
| 1 g thiamine | |
| SB55 (per L) | |
| 10 mL each MS stocks | |
| 1 mL B5 Vitamin stock | |
| 0.8 g $NH_4NO_3$ | |
| 3.033 g $KNO_3$ | |
| 1 mL 2,4-D (10 mg/mL stock) | |
| 60 g sucrose | |
| 0.667 g asparagine | |
| pH 5.7 | |
| SBP6 (per L) 0.5 mL 2,4-D in SB55 | |
| SB103 (per L) | |
| MS Salts | |
| 6% maltose | |
| 750 mg $MgCl_2$ | |
| 0.2% Gelrite | |
| pH 5.7 | |

EXAMPLE 9

AGROBACTERIUM MEDIATED TRANSFORMATION

Tobacco transformation

The binary vectors pKR12, p2STE1, and pPHTE were transferred by a freeze/thaw method (Holsters et al., Mol Gen Genet (1978) 163:181–187) to the Agrobacterium strain LBA4404/pAL4404 (Hockema et al., Nature (1983) 303:179–180). The Agrobacterium transformants were used to inoculate tobacco leaf disks (Horsch et al., Science (1985)

227:1229–1231). Transgenic plants were regenerated in selective media containing kanamycin.

Brassica napus transformation

Seeds of cultivar *B. napus* Wester were surface sterilized with a solution of 10% Clorox®, 0.1% SDS and placed on germination media consisting of 30 mM $CaCl_2$, 1.5% agar for 5 to 7 days.

Three mL cultures of *Agrobacterium tumafaciens* (strain LBA 4404) containing the desired binary vector constructions were grown for 18 to 20 h in Min A media at 28° C. To begin the transformation, plates of co-cultivation media (BC-1 with 100 μM acetosyringone) were poured and allowed to air-dry in a laminar flow hood. Seedling hypocotyls were cut into 1 cm segments and placed into 22.5 mL of bacterial dilution medium (MS liquid media with 100 μM acetosyringone). To the solution containing the hypocotyl segments was added 2.5 mL of the overnight culture of Agrobacterium. After 30 min the hypocotyl segments were removed and placed, 10 per plate, on the co-cultivation media plates. The plates were then incubated at 25° C. for three days in dim light.

After three days the segments were transferred to selective media plates (BC-1 media with 200 mg/L carbenicillin and 50 mg/mL kanamycin). Callus growth occurred at the cut ends of the hypocotyls over the next 20 days, and after 20 days calli greater than 5 mm in diameter were transferred to selective regeneration media (BS-49 containing 200 mg/L carbenicillin). At the same time, the remaining hypocotyl segments were transferred to fresh selective media and addition calli developing over the next 15 days were also transferred to the selective regeneration media. All calli produced were thus transferred to selective regeneration media by 72 days after the co-cultivation with Agrobacterium.

Individual calli on selective regeneration media were maintained in continuous light at 25° C., and placed on fresh media at two week intervals. If no shoot primordia appeared after six weeks on the regeneration media, the calli were chipped into 5 mm pieces, re-plated on BC-1 media containing 200 mg/L carbenicillin for three days, then transferred back to BS-48 media with 200 mg/L carbenicillin. Shoots appeared three to six weeks after calli were transferred to BS-48 media.

Shoots formed on BS-48 were allowed to elongate somewhat before excision and plating on MSVA-1A media. Shoots were transferred to fresh MSVA-1A media for a second, three-week cycle before transplanting directly into potting mix.

| Media (amounts/L) |
|---|
| BC-1MS minimal organic salts medium (MS salts + 100 mg/L i-inositol and 0,4 mg/mL thiamine) |

30 g sucrose
18 g mannitol
3 mg Kinetin
3 g DNA grade Agarose
adjusted to pH 5.8

BS-48

MS minimal Organic Medium (as above)
B5 vitamines (1 mL of 1000× stock, described above)
250 mg xylose
10 g glucose
0.6 g MES
4 g DNA grade agarose adjust to pH 5.7 and add from sterile solutions after autoclaving; 2 mg Zeatin and 0.1 mg indole acetic acid

| MSVA-1A |
|---|
| MS minimal organic salts medium
10 g sucrose
B5 vitamins (1 mL of 1000× stock, described above)
6 g DNA grade agarose
adjust to pH 5.8 |

EXAMPLE 10

ANALYSIS OF TRANSGENIC PLANTS

Analysis of Somatic Soybean Embryos

While in the globular embryo state in liquid culture as described in Example 8, somatic soybean embryos contain very low amounts of triacylglycerol or storage proteins typical of maturing, zygotic soybean embryos. At this developmental state, the ratio of total triacylglyceride to total polar lipid (phospholipids and glycolipid) was about 1:4, as is typical of zygotic soybean embryos at the developmental stage from which the somatic embryo culture was initiated. At the globular stage as well, the mRNAs for the prominant seed proteins α' subunit of β-conglycinin, Kunitz Trypsin Inhibitor III and Soybean Seed Lectin were essentially absent. Upon transfer to hormone-free, solid media to allow differentiation to the maturing somatic embryo state as described in Example 8, triacylglycerol became the most abundant lipid class. Similarly, mRNAs for α'-subunit of β-conglycinin, Kunitz Trypsin Inhibitor III and Soybean Seed Lectin became very abundant messages in the total mRNA population. In these respects, the somatic soybean embryo system behaves very similarly to maturing zygotic soybean embryos in vivo, and is therefore a good and rapid model system for analyzing the phenotypic effects of modifying the expression of genes in the fatty acid biosynthesis pathway such as acyl-ACP thioesterase and for predicting the alterations expected in zygotic embryos. Similar zygotic embryo culture systems have been documented and used in another oilseed crop, rapeseed (Taylor et al., Planta (1990) 181:18–26).

Assay for in vitro thioesterase activity from globular stage somatic soybean cultures of Example 8

Uniform clumps from eighteen of the twenty-one transformed lines obtained in Example 8 along with 3 non-transformed controls, were placed in tared, 1.5 mL microfuge tubes and re-weighed to obtain the tissue fresh weight. Two times the tissue weight in an extraction buffer consisting of 0.1M Tricine (pH 8.2), 0.5 mM EDTA and 1 mM DTT was added and the tissue piece was homogenized with a small pestle. The homogenate was centrifuged to clear and 2 μL of the supernatant was added to an assay mixture consisting of 35 μL of the above Tricine buffer also containing 1 mg BSA/mL and 1 μM [$^{14}$C]-oleoyl-ACP (58 mCi/mmol). The reaction was stopped after 2 min by the addition of 100 μL of 10% acetic acid in 2-propanol. Hydrolyzed, $^{14}$C-oleate was extracted from the mixture by two, 1 mL extractions with water-saturated hexane and taken for scintillation counting. Extracted protein was determined by the Bradford assay (Biorad) using 2 μL of the extract. The results of these assays are shown in Table 4.

TABLE 4

| CULTURE LINE IDENTIFICATION | THIOESTERASE SPECIFIC ACTIVITY (nmol · mg protein$^{-1}$ min$^{-1}$) |
|---|---|
| Control | 0.92 |
| Control | 1.21 |
| Control | 1.08 |
| 194-5/4 | 0.69 |
| 194-6/5 | 0.75 |
| 294-6/1 | 0.39 |
| 194-3,5,6-1 | 0.30 |
| 194-5/2 | 0.34 |
| 194-6/4 | 0.88 |
| 194-5/1 | 0.76 |
| 194-3,5,6-2 | 0.78 |
| 194-3,4,6-3 | 0.39 |
| 194-1/2 | 0.73 |
| 194-4/1 | 0.41 |
| 194-2/2 | 1.12 |
| 194-6/2 | 1.09 |
| 194-6/3 | 0.92 |
| 194-1/4 | 0.15 |
| 194-1/1 | 0.38 |
| 194-5/3 | 0.88 |
| 194-5/5 | 0.20 |

These results were unexpected because the acyl-ACP thioesterase gene was introduced in such a manner as to encode the sense message from the gene and therefore the production of additional acyl-ACP thioesterase protein and corresponding additional enzymatic activity. In the introduction of a gene into tissue in which that same gene or one very highly homologous to it is expressed, cosuppressive inhibition of both messages is a possibility. Another factor which was considered is that the control tissue in this experiment was not transformed and grown on the selective media as described in Example 8. It is possible that the selective media suppresses thioesterase activity and that the controls utilized were improper. To test for this possibility tissue clumps from the selected, transformed lines were removed from media containing the selective agent (hydromycin) and allowed to re-grow in liquid culture. Assays were again performed as described above. The result was identical: no transformed lines exhibited thioesterase-specific activities higher than control cultures. When the thioesterase specific activities for transformed lines grown on selective media was plotted against the specific activity for the same line grown without hydromycin the correlation coefficient was 0.85. It is logical to conclude that the suppression of acyl-ACP thioesterase activity is a function of transformation.

Northern analysis of selected lines of transformed soybean somatic embryo cultures Nine of the twenty-one somatic embryo lines chosen as representative of lines with greatly decreased acyl-ACP thioesterase-specific activity, of lines with only moderately decreased activity, and of lines which do not appear to be different from untransformed controls were grown for further study. Total RNA was obtained from transformed soybean somatic embryo cultures by the Pheno/SDS Method (Current Protocols in Molecular Biology, Ed. F. M. Ausubel et al., (1991) John Wiley and Sons, pg. 4,3,1–4,3,3).

Poly A+mRNA was isolated by oligo dT affinity chromatography as described by Aviv et al. (Proc. Nat. Acad. Sci. U.S.A. (1972) 69:1408–1412. Two µg of polyA+ mRNA was separated from each transformed soybean culture line in a denaturing formaldehyde gel for an RNA blot analysis as described by Lehrach et al. (Biochemistry (1977) 16:4743–4749). Standards containing known amounts of pure acyl-ACP thioesterase mRNA were included in the gel for quantitation of acyl-ACP thioesterase mRNA in the transgenic lines. The standard was synthesized in nitro using the method of Krieg et al., Nucl. Acids Res. (1984) 12:7057–7070) with p22B as the template DNA. The gel-separated mRNA was transferred to Nytran filter and hybridized with $^{32}$P-labelled soybean thioesterase RNA probes as described by Berger et al. (Methods Enzymol. (1987) 152:577–582), again using p22B as the template. Hybridization was at 68° C. in 50% formamide, 0.5M NaCl, 10x Denhardt's, 0.2% SDS, 250 µg/mL yeast RNA. The filter was washed at 68° C. once in 2×SSC 30 min and four times in 0.2×SSC at 68° C. 30 min each. The filter was exposed to X-ray film overnight at −80° C. with a DuPont Cronex® intensifying screen.

The construction of pKR12 (see Example 7) deletes a portion of the 5' untranslated region of the soybean seed acyl-ACP thioesterase message. As a result, the expected message size for expressed acyl-ACP thioesterase transgene is about 200 base pairs smaller than the message from expressed endogenous genes. In all nine lines a message of about 1.6 kB in size was present in the somatic soybean embryos. In all but line 194-6/3 a second message of about 1.4 kB in size was also present. After probing with the acyl-ACP thioesterase probe, the blots were stripped of labelling by continued washing as above and re-probed with [$^{32}$P]-RNA prepared as described above but using a Bluescript plasmid containing the cDNA for soybean seed Oleosin in the insert. The oleosin message is highly expressed in the somatic soybean embryos and was used to normalize the amount of mRNA loaded from each line. The two lines expressing greatly reduced acyl-ACP thioesterase activity (194-5/5 and 194-1/4) also had greatly reduced levels of both the transgene acyl-ACP thioesterase message and the endogenous acyl-ACP thioesterase message. Lines 194-2/4 and 194-5/4 had slightly reduced levels of both messages although it appeared that the endogenous message was decreased in relation to the transgene message. The level of both messages was somewhat lower in line 194-5/4 than in line 194-2/4. Line 194-6/3 had only the endogenous message but lines 194-6/4 and 194-6/5 had high levels of both the transgene and endogenous gene messages, while all three of these lines had acyl-ACP thioesterase activities at or near the wildtype level. The single message signal in 194-6/3 is explained by the lack of an introduced acyl-ACP thioesterase gene in this line (see Southern analysis below) but the lack of effect of the expressed acyl-ACP thioesterase message in lines 194-6/4 and 194-6/5 is not simply explained. The reduced message levels in the remaining lines correlates exactly with reduced acyl-ACP thioesterase activity and are diagnostic of co-suppression as seen when highly homologous messages of slightly differing size are produced (van der Krol et al., The Plant Cell (1990) 2:291–299).

The sequence of SEQ ID NO:1 or any nucleic acid fragment substantially homologous therewith is therefore shown to be effective in reducing acyl-ACP thioesterase activity by cosuppression when re-introduced into soybean and expressed in an appropriate expression vector.

Southern analysis of genomic DNA from transformed somatic soybean embryos

Genomic DNA was isolated from maturing somatic embryos from the 7 surviving lines described below and digested with XbaI as described in Example 3. Southern analysis was also done as in Example 3 using either the acyl-ACP thioesterase coding sequence as the probe template or the neomycin phosphotransferase coding sequence as the probe template. Using the coding sequence of acyl-ACP thioesterase as the probe revealed that all lines except 194-6/3 contained introduced copies of the sequence in addition to the endogenous copies. All lines except 194-5/5 had at least one copy which was not rearranged form the introduced pKR12 construction. Line 194-5/5 had multiple inserts, all of which had undergone some rearrangement. Probing with the neomycin phosphotransferase coding sequence showed that all transformed lines had at least one copy of the selectable marker. Occurrence of copies ranged from one in the case of line 194-6/3 to eight in the case of line 194-5/5.

Analysis of fatty acid profiles and triacylglycerol synthesis in transformed soybean somatic embryos Seven of the transformed lines from Example 8 were successfully grown on solid, hormone free, maturation media. These lines were used for growth rate analysis, analysis of the rate of triacylglycerol synthesis, and analysis of the fatty acid profile of the triacylglycerol.

esters were re-dissolved in between 50 and 200 µL of hexane (depending on the embryo age) for analysis by GLC. GLC separations were done isothermally at 185° on a fused silica capillary column (stationary phase, SP- 2330, 30M in length, Supelco, Bellefonte, Pa.). Data were analyzed by integration relative to the assigned weight of the internal standard peak to determine both the absolute weight of total fatty acids in triacylglycerol and the relative contribution of each of the five most prominant fatty acids in soybean triacylglycerol.

The specific activity of acyl-ACP thioesterase was also analyzed in the maturing embryos at mid-maturation by the method described above. The relative contributions of individual fatty acids to the total fatty acid profile, total amount of triacylglyceride synthesized, and the specific activity of the acyl-ACP thioesterase for the seven transformed lines and one untransformed control are given in Table 5.

TABLE 5

| Cell Line | % of Total Fatty Acids | | | | | Total Triacyl-glycerol (% dry wt.) | Thioesterase Sp. Activity (nmol · mg$^{-1}$ min$^{-1}$) |
|---|---|---|---|---|---|---|---|
| | 16:0 | 18:0 | 18:1 | 18:2 | 18:3 | | |
| Control | 14.9 | 3.5 | 9.9 | 56.6 | 15.0 | 5.7 | 1.07 |
| 194-6/3 | 16.5 | 3.4 | 9.8 | 50.8 | 18.9 | 5.8 | 1.06 |
| 194-6/4 | 23.8 | 3.0 | 9.1 | 56.6 | 26.5 | 7.6 | 0.98 |
| 194-6/5 | 11.1 | 2.9 | 10.7 | 57.0 | 15.6 | ND | 0.80 |
| 194-2/4 | 13.2 | 2.7 | 20.6 | 59.1 | 13.6 | 6.2 | 0.70 |
| 194-5/4 | 9.8 | 3.0 | 11.0 | 57.8 | 16.8 | 6.9 | 0.64 |
| 194-1/4 | 17.4 | 3.7 | 7.6 | 51.5 | 19.6 | 3.6 | 0.24 |
| 194-5/5 | 17.82 | 4.6 | 4.7 | 46.2 | 25.8 | 2.4 | 0.22 |

Following placement on the maturation media and subsequent differentiation of the globular embryo culture into the maturing embryos, four replicate samples of five embryos each per line were taken at intervals. The length of time to differentiation varied with culture line, but embryos produced by each line were of very similar fresh and dry weights at the point of differentiation. This point, at which differentiated embryos could be easily removed from the remaining globular culture was designated as "time 0" in the course of triacylglycerol synthesis and dry weight accumulation.

Embryos from each line and time point were weighed for fresh weight, lyophilized and re-weighed for dry weight and lipid extraction. An internal standard of tri-heptadecanoyl glycerol was prepared by reacting the acid chloride of heptadecanoic acid with glycerol in dimethylformamide (DMF) with triethyl amine. The triacylglyceride was purified by passage through silica, crystalized from diethyl ether and used to make a 0.5 mg.m$^{-1}$ standard solution in 2-propanol. Addition of 100 µL of the standard solution to the extraction solvent for each sample gave an internal standard of 50 µg which was co-purified, derivatized and chromatographed with the extracted lipid. In addition to the internal standard solution, the embryos were ground in 0.5 mL of diethyl ether and centrifuged. The ether layer was removed and the extraction was repeated. The combined extracts were passed through a prepared silica column (Sep Pak silica cartridge, Millipose) and the neutral lipid fraction was eluted with 2 mL of diethyl ether. The column eluate was taken to dryness under an N$_2$ stream and neutral lipids in the residue were transesterified to methanol in 0.5 mL of 1% sodium methoxide in methanol. One mL of a saturated NaCl solution was added and the fatty acid methyl esters were extracted into diethyl ether. The ether solutions were taken to dryness under an N$_2$ stream and the extracted methyl The fatty acid profile values in Table 5 are the means of four to six determinations. The thioesterase specific activities are the means of three assays, two done at the globular tissue stage and one at the developing embryo stage.

The results show that the nucleotide sequence of SEQ ID NO:1 is effective in altering seed storage lipid biosynthesis. Moderate reduction of the acyl-ACP thioesterase activity does reduce the level of saturated fatty acid in triacylglycerol (the 16:0 value for line 194-5/4 is significantly lower than the control values). Fold reduction of the acyl-ACP thioesterase activity in the range of 5 or greater leads to additional effects; the total accumulation of triacylglycerol was significantly decreased and it is likely that the rate of triacylglycerol synthesis was also decreased.

Analysis of tobacco transformed with constituative and seed specific constructions Tobacco plants transformed with pKZ12, pKZ13, p2STE1, and pPHTE1 (see Example 9) were analyzed for acyl-ACP thioesterase activity. Those plants transformed with the constitutive constructs pKZ12 and pKZ13 were analyzed at the callus level, at the seedling stage just after transfer to pots, and in the developing seeds. Seven developing plants were obtained from transformations with pKR12 and six from transformations with pKR13. Of the seven pKR12 transformants, two showed acyl-ACP thioesterase specific activity that was higher than control plants in very young seedlings. One of those plants (KR12-4B) maintained measurably higher levels of thioesterase activity in developing seeds. Tobacco seeds undergo a marked, developmental change in seed acyl-ACP-thioesterase activity. Since it is difficult to determine seed developmental age with accuracy, determining increased thioesterase activity relative to controls is also imprecise. Nevertheless, it appeared that plant KR12-4B retained about a two-fold increased acyl-ACP thioesterase specific activity in the seeds. Twenty-two immature seeds from the segregating population of seeds on KR12-4B were individually assayed for thioesterase activity on a per seed basis. Three individuals of the twenty-two had acyl-ACP thioesterase activity in the range of 1.2 to 1.7 nmol/10 min/seed. Five seeds had activity in the range from 3.3 to 3.9 nmol/10 min/seed, while the remaining fourteen fell in the range between 2 and 3 nmol/10 min/seed. This ratio is reasonably near the 1:2:1 ratio that would be predicted for the segregating population from a single effective transgene insert if each gene dose of the transgene gives acyl-ACP thioesterase activity. approximately equal to that from the endogenous gene in this plant.

Eleven tobacco plants transformed with p2STE1 and six tobacco plants transformed with pPHTE1 have been assayed for acyl-ACP thioesterase activity in developing seeds. Of the p2STE1 transformed plants, five did not appear to be different from wildtype in activity, three were clearly higher than wildtype and three others were not at developmental stages which allowed comparison. The three transformants which had higher activity were judged to have 1.9, 2.0 and 2.6 times the acyl-ACP thioesterase-specific activity of untransformed controls at an equivalent developmental stage. Of the six pPHTE1 transformants assayed, two could not be compared reliably due to their immature developmental stage, two were approximately equal to wild-type, and two had higher activity. These two lines measured 2.5 and 2.9 fold higher than equivalent control seeds.

Applicants have shown that either constitutive or seed specific expression of the soybean seed acyl-ACP thioesterase gene in a plant may give increased acyl-ACP thioesterase activity provided that endogenously expressed acyl-ACP thioesterases are not excessively homologous to the introduced gene.

Analysis of transformed *Brassic napus*

*Brassica napus* transformed with pKR13 as described in Example 9 was analyzed for acyl-ACP thioesterase specific activity at the stage of transformed callus after re-induction on hormonal media as described in Example 9. Calli from twenty-eight individual transformants along with four control calli were assayed by grinding the callus with a pestle in a 1.5 mL microfuge tube after addition of a buffer concentrate consisting of 10 μL of 0.1M Tricine, pH 8 and 10 mM DTT. The homogenate was centrifuged to clear and 5 μL of the supernatant was used in the acyl-ACP thioesterase assay as described above. The assay value for each transformant was compared to the control average and then placed in classes of 10% intervals to produce frequency distribution. See Table 6.

TABLE 6

| CLASS (% of control) | FREQUENCY |
| --- | --- |
| 110–90 | 7 |
| 89–80 | 3 |
| 79–70 | 4 |
| 69–60 | 7 |
| 59–50 | 2 |
| 49–40 | 1 |
| 39–30 | 1 |
| 29–20 | 3 |

What is claimed is:

1. An isolated nucleic-acid fragment comprising a nucleotide sequence encoding an acyl-ACP thioesterase, wherein said thioesterase catalyzes the hydrolysis of palmitoyl, stearoyl and oleoyl-ACP thioesters, and wherein said thioesterase has the amino acid sequence of the mature functional protein encoded by nucleotides 271 to 1206 of SEQ ID NO:1 or 282 to 1217 of SEQ ID NO: 3 or any nucleotide sequence encoding said mature functional protein in which one or more amino acid substitutions have been made that do not affect the functional properties of the thioesterase.

2. An isolated nucleic acid fragment of claim 1 wherein said fragment is isolated from soybean.

3. An isolated nucleic acid fragment comprising a nucleotide sequence encoding the soybean seed acyl-ACP thioesterase cDNA corresponding to the nucleotides 1 to 1602 of SEQ ID NO:1.

4. An isolated nucleic acid fragment comprising a nucleotide sequence encoding the soybean seed acyl-ACP thioesterase cDNA corresponding to the nucleotides 1 to 1476 of SEQ ID NO:3.

5. An isolated nucleic acid fragment wherein said nucleotide sequence encodes the soybean seed acyl-ACP thioesterase precursor corresponding to nucleotides 106 to 1206 of SEQ ID NO:1.

6. An isolated nucleic acid fragment wherein said nucleotide sequence encodes the soybean seed acyl-ACP thioesterase precursor corresponding to nucleotides 117 to 1217 of SEQ ID NO:3.

7. An isolated nucleic acid fragment wherein the said nucleotide sequence encodes the mature soybean seed acyl-ACP thioesterase enzyme corresponding to nucleotides 271 to 1206 of SEQ ID NO:1.

8. An isolated nucleic acid fragment wherein the said nucleotide sequence encodes the mature soybean seed acyl ACP thioesterase enzyme corresponding to nucleotides 282 to 1217 of SEQ ID NO:3.

9. A chimeric gene causing altered levels of acyl-ACP thioesterase activity in a transformed plant cell, the gene comprising a nucleic acid fragment of claim 1 operably linked either in sense orientation or in antisense orientation to suitable regulatory sequences.

10. A plant cell transformed with the chimeric gene of claim 9.

11. A method of producing seed oil containing altered levels of palmitic and stearic acids comprising:

(a) transforming a plant cell of an oil-producing species with a chimeric gene of claim 9, (b) growing fertile plants from the transformed plant cells of step (a), (c) screening progeny seeds from the fertile plants of step (b) for the desired levels of palmitic and stearic acids, and (d) processing the progeny seed of step (c) to obtain oil containing altered levels of palmitic and stearic acids.

12. A method of claim 11 wherein the plant cell of an oil-producing species is selected from the group consisting of soybean, oil seed Brassica species, sunflower, cotton, cocoa, peanut, safflower, and corn.

13. A chimeric gene causing reduced levels of mature seed acyl-ACP thioesterase activity in a transformed soybean plant the gene comprising a nucleic acid fragment of claim 1 operably linked in a sense 5' to 3' direction to suitable regulatory sequences wherein expression of the nucleic acid fragment results in co-suppression of endogenous thioesterase activity.

14. A chimeric gene causing increased levels of mature seed acyl-ACP thioesterase activity in a transformed plant, wherein said plant is not soybean, the gene comprising a nucleic acid fragment of claim 1 operably linked to suitable regulatory sequences.

15. A transformed soybean plant having lowered levels of acyl-ACP thioesterase activity comprising an endogenous acyl-ACP thioesterase gene and the chimeric gene of claim 13.

16. A method of producing soybean seed oil containing reduced levels of palmitic and stearic acids comprising:

(a) transforming a soybean plant cell with a chimeric gene of claim 13, (b) growing fertile soybean plants from the transformed plant cells of step (a), (c) screening progeny seeds form the fertile soybean plants of step (b) for the desired reduced levels of palmitic and stearic acids, and (d) processing the progeny seed of step (c) to obtain oil containing reduced levels of palmitic and stearic acids.

17. A chimeric gene causing reduced levels of mature seed acyl-ACP thioesterase activity in a transformed soybean plant the gene comprising a nucleic acid fragment of claim 1 operably linked in an antisense 3' to 5' direction to suitable regulatory sequences wherein expression of the nucleic acid fragment results in antisense inhibition of endogenous thioesterase activity.

18. A method of producing soybean seed oil containing reduced levels of palmitic and stearic acids comprising:

(a) transforming a soybean plant cell with sequence ID No. 1 operably linked, in antisense orientation, to suitable transcription regulatory sequences, (b) growing fertile soybean plants from the transformed plant cells of step (a), (c) screening progeny seeds from the fertile soybean plants of step (b) for the desired reduced levels of palmitic and stearic acids, and (d) processing the progeny seed of step (c) to obtain oil containing reduced levels of palmitic and stearic acids.

19. A chimeric gene causing increased levels of mature seed acyl-ACP thioesterase activity in a transformed plant the gene comprising a nucleic acid fragment of claim 1 operably linked in a sense 5' to 3' direction to suitable regulatory sequences.

20. A method of producing plant oil containing increased levels of palmitic and stearic acids comprising:

(a) transforming a plant cell, other than a soybean plant cell, with a chimeric gene of claim 19, (b) growing fertile plants from the transformed plant cells of step (a), (c) screening progeny seeds from the fertile plants of step (b) for the desired increased levels of palmitic and stearic acids, and (d) processing the progeny seed of step (c) to obtain oil containing increased levels of palmitic and stearic acids.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
      ( A ) LENGTH: 1602 base pairs
      ( B ) TYPE: Nucleic acid
      ( C ) STRANDEDNESS: single
      ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
      ( A ) ORGANISM: Glycine max
      ( B ) STRAIN: Cultivar Wye
      ( D ) DEVELOPMENTAL STAGE: Early seed fill
      ( E ) HAPLOTYPE: Diploid
      ( F ) TISSUE TYPE: Cotyledon
      ( I ) ORGANELLE: Nucleus ( v i i ) IMMEDIATE SOURCE:
      ( A ) LIBRARY: cDNA to mRNA
      ( B ) CLONE: 22B ( i x ) FEATURE:
      ( A ) NAME/KEY: mat_peptide
      ( B ) LOCATION: 271..1206
      ( C ) IDENTIFICATION METHOD: Catalytically active when expressed in E. coli ( i x ) FEATURE:
  ( A ) NAME/KEY: CDS
  ( B ) LOCATION: 106..1209

( x i ) SEQUENCE DESCRIPTION: SEQ ID NO:1:

```
CCTTCTTTCT CATTCTCATA CGCACCCAGT CACCCAGCTT TCCCTTTTTC CTATTTTTT        60

TCTCTTTTTT TATTAAAAAA ATAAAAATGT TGAAGCTTTC GTGCA ATG GCT TGG          114
                                                  Met Ala Trp
                                                   -55

ACC GGG CTC ACT CCC TGG CCC AAT GCG CTT CCG GGC CGG CCC GCC TGC        162
Thr Gly Leu Thr Pro Trp Pro Asn Ala Leu Pro Gly Arg Pro Ala Cys
        -50             -45                 -40

GCC GTC CCT CGC CGG AGG AGG AGC GGC GTC TCC GGA TTC CGG TTG CCG        210
Ala Val Pro Arg Arg Arg Arg Ser Gly Val Ser Gly Phe Arg Leu Pro
-35                 -30                 -25

GAA GGC AGG TCG ATC CGG GTG TCC GCG GCG GTG TCG GCA AAG GAC GGC        258
Glu Gly Arg Ser Ile Arg Val Ser Ala Ala Val Ser Ala Lys Asp Gly
-20                 -15                 -10                  -5

GCG GTG GCG ACC CGG GTA GAG GCG GAT CCC GGT ACG CTG GCG GAC CGG        306
Ala Val Ala Thr Arg Val Glu Ala Asp Pro Gly Thr Leu Ala Asp Arg
                  1                 5                  10

CTG AGG GTG GGG AGC TTG ACG GAG GAT GGG TTG TCT TAT AAG GAG AAG        354
Leu Arg Val Gly Ser Leu Thr Glu Asp Gly Leu Ser Tyr Lys Glu Lys
         15                 20                  25

TTC ATT GTG AGG AGC TAC GAA GTT GGG ATC AAT AAG ACT GCC ACT GTT        402
Phe Ile Val Arg Ser Tyr Glu Val Gly Ile Asn Lys Thr Ala Thr Val
         30                 35                  40

GAA ACC ATT GCC AAT CTC TTG CAG GAG GTT GGA TGT AAT CAT GCT CAG        450
Glu Thr Ile Ala Asn Leu Leu Gln Glu Val Gly Cys Asn His Ala Gln
 45                 50                 55                   60

AGT GTT GGA TAT TCT ACT GAT GGT TTT GCA ACC ACC CCT ACG ATG AGA        498
Ser Val Gly Tyr Ser Thr Asp Gly Phe Ala Thr Thr Pro Thr Met Arg
                 65                  70                   75

AAA TTG CGT CTC ATA TGG GTT ACT GCT CGC ATG CAC ATT GAA ATC TAC        546
Lys Leu Arg Leu Ile Trp Val Thr Ala Arg Met His Ile Glu Ile Tyr
             80                  85                  90

AAA TAC CCT GCT TGG AGT GAC ATT GTT GAG ATA GAG ACA TGG TGC CAA        594
Lys Tyr Pro Ala Trp Ser Asp Ile Val Glu Ile Glu Thr Trp Cys Gln
         95                 100                 105

GGG GAA GGA AGG GTT GGG ACA AGG CGT GAT TTT ATA CTG AAA GAC TAT        642
Gly Glu Gly Arg Val Gly Thr Arg Arg Asp Phe Ile Leu Lys Asp Tyr
110                 115                 120

GCA ACT GAT GAA GTT ATT GGA AGG GCA ACA AGC AAA TGG GTA ATG ATG        690
Ala Thr Asp Glu Val Ile Gly Arg Ala Thr Ser Lys Trp Val Met Met
125                 130                 135                 140

AAT CAG GAC ACC AGA CGA CTC CAG AAG GTT TCT GAT GAT GTT AAA GAA        738
Asn Gln Asp Thr Arg Arg Leu Gln Lys Val Ser Asp Asp Val Lys Glu
                145                 150                 155

GAG TAT TTG GTT TTC TGT CCT CGA GAG CCC AGG TTA GCT ATT CCA GAG        786
Glu Tyr Leu Val Phe Cys Pro Arg Glu Pro Arg Leu Ala Ile Pro Glu
            160                 165                 170

GCA GAT AGT AAT AGC TTG AAG AAA ATA CCA AAA TTG GAA GAC CCT GCT        834
Ala Asp Ser Asn Ser Leu Lys Lys Ile Pro Lys Leu Glu Asp Pro Ala
        175                 180                 185

CAG TAT TCC AGA CTT GGA CTT GTG CCA AGA AGA GCG GAT CTG GAC ATG        882
Gln Tyr Ser Arg Leu Gly Leu Val Pro Arg Arg Ala Asp Leu Asp Met
    190                 195                 200

AAT CAG CAT GTT AAC AAT GTC ACC TAT ATT GGA TGG GTG CTT GAG AGC        930
Asn Gln His Val Asn Asn Val Thr Tyr Ile Gly Trp Val Leu Glu Ser
205                 210                 215                 220
```

```
ATG CCT CAA GAA ATC ATT GAT AGC CAT GAG TTG CAG AGT ATT ACC TTG          978
Met Pro Gln Glu Ile Ile Asp Ser His Glu Leu Gln Ser Ile Thr Leu
            225             230                 235

GAT TAC AGA CGA GAG TGC GGA CAA CAT GAC ATA GTC GAT TCC CTC ACT         1026
Asp Tyr Arg Arg Glu Cys Gly Gln His Asp Ile Val Asp Ser Leu Thr
            240             245                 250

AGT GTG GAA GCG ATA CAG GGT GGT GCC GAG GCA GTT CCA GAA CTG AAA         1074
Ser Val Glu Ala Ile Gln Gly Gly Ala Glu Ala Val Pro Glu Leu Lys
            255             260                 265

GGT ACA AAT GGA TCT GCC ACG GCA AGG GAA GAC AAA CAT GAA CAC CAG         1122
Gly Thr Asn Gly Ser Ala Thr Ala Arg Glu Asp Lys His Glu His Gln
            270             275                 280

CAG TTT CTG CAT CTA CTT AGG TTG TCT ACT GAA GGA CTT GAG ATA AAC         1170
Gln Phe Leu His Leu Leu Arg Leu Ser Thr Glu Gly Leu Glu Ile Asn
285             290                 295                 300

CGG GGA CGA ACA GAA TGG AGA AAG AAA GCT CCA AGA TGAGAACCAT              1216
Arg Gly Arg Thr Glu Trp Arg Lys Lys Ala Pro Arg
                305                 310

TATGTGTGCT TCCACCCGAA TCCATGATTC TGTTTTTGTC TTGTGTTGTT TCATGTTACC       1276

AGGGTTGTCT TATCAATTTT CCCTTGATAT TTTGCTTAGA GTTTGTGCGC TTAATAGGGA       1336

TTGAAGAGTT AAAATATTGC TTCTGTTTTC TTGTCATGCT GATCAAAAAT TTAAGTTGTC       1396

CAAATCCCGT AGTTAGGCTA TATAGGTTGA CATCAATCTC TGATCCATTA GTATCAGATT       1456

CCATGAATGT CATTGTACCT TAAGGGAGCA TAGAAATCCA GGAAGTTGGT ATGGATCTGC       1516

CATCTACTGC ATGACTTGAA CAATGTGTGT TAAAATAATC ATTTTGAAAT AATTCAATTA       1576

GCTAATTATT AATGTTCTTA AAAAAA                                            1602
```

(2) INFORMATION FOR SEQ ID NO:2:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Trp Thr Gly Leu Thr Pro Trp Pro Asn Ala Leu Pro Gly Arg
-55             -50                 -45                 -40

Pro Ala Cys Ala Val Pro Arg Arg Arg Ser Gly Val Ser Gly Phe
                -35                 -30                 -25

Arg Leu Pro Glu Gly Arg Ser Ile Arg Val Ser Ala Ala Val Ser Ala
            -20             -15                 -10

Lys Asp Gly Ala Val Ala Thr Arg Val Glu Ala Asp Pro Gly Thr Leu
        -5                   1                  5

Ala Asp Arg Leu Arg Val Gly Ser Leu Thr Glu Asp Gly Leu Ser Tyr
 10              15                  20                  25

Lys Glu Lys Phe Ile Val Arg Ser Tyr Glu Val Gly Ile Asn Lys Thr
                30                  35                  40

Ala Thr Val Glu Thr Ile Ala Asn Leu Leu Gln Glu Val Gly Cys Asn
             45                  50                  55

His Ala Gln Ser Val Gly Tyr Ser Thr Asp Gly Phe Ala Thr Thr Pro
         60                  65                  70

Thr Met Arg Lys Leu Arg Leu Ile Trp Val Thr Ala Arg Met His Ile
     75                  80                  85

Glu Ile Tyr Lys Tyr Pro Ala Trp Ser Asp Ile Val Glu Ile Glu Thr
 90                  95                 100                 105
```

| | | | | | | | | | | | | | |
|---|---|---|---|---|---|---|---|---|---|---|---|---|---|
|Trp|Cys|Gln|Gly 110|Glu|Gly|Arg|Val|Gly Thr 115|Arg|Arg|Asp|Phe|Ile Leu 120|
|Lys|Asp|Tyr|Ala 125|Thr|Asp|Glu|Val|Ile Gly 130|Arg|Ala|Thr|Ser 135|Lys Trp|
|Val|Met|Met 140|Asn|Gln|Asp|Thr|Arg 145|Arg Leu|Gln|Lys|Val 150|Ser|Asp Asp|
|Val|Lys 155|Glu|Glu|Tyr|Leu|Val 160|Phe|Cys Pro|Arg|Glu 165|Pro|Arg|Leu Ala|
|Ile 170|Pro|Glu|Ala|Asp|Ser 175|Asn|Ser|Leu Lys|Lys 180|Ile|Pro|Lys|Leu Glu 185|
|Asp|Pro|Ala|Gln|Tyr 190|Ser|Arg|Leu|Gly Leu 195|Val|Pro|Arg|Arg|Ala Asp 200|
|Leu|Asp|Met|Asn 205|Gln|His|Val|Asn|Asn Val 210|Thr|Tyr|Ile|Gly 215|Trp Val|
|Leu|Glu|Ser 220|Met|Pro|Gln|Glu|Ile 225|Ile Asp|Ser|His|Glu 230|Leu|Gln Ser|
|Ile|Thr 235|Leu|Asp|Tyr|Arg|Arg 240|Glu|Cys Gly|Gln|His 245|Asp|Ile|Val Asp|
|Ser 250|Leu|Thr|Ser|Val|Glu 255|Ala|Ile|Gln Gly|Gly 260|Ala|Glu|Ala|Val Pro 265|
|Glu|Leu|Lys|Gly|Thr 270|Asn|Gly|Ser|Ala Thr 275|Ala|Arg|Glu|Asp|Lys His 280|
|Glu|His|Gln|Gln 285|Phe|Leu|His|Leu|Leu Arg 290|Leu|Ser|Thr|Glu 295|Gly Leu|
|Glu|Ile|Asn 300|Arg|Gly|Arg|Thr|Glu 305|Trp Arg|Lys|Lys|Ala 310|Pro|Arg|

(2) INFORMATION FOR SEQ ID NO:3:

(i) SEQUENCE CHARACTERISTICS:
        (A) LENGTH: 1476 base pairs
        (B) TYPE: Nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Glycine max
        (B) STRAIN: Cultivar Wye
        (D) DEVELOPMENTAL STAGE: Early seed fill
        (E) HAPLOTYPE: Diploid
        (F) TISSUE TYPE: Cotyledon
        (I) ORGANELLE: Nucleus (vii) IMMEDIATE SOURCE:
        (A) LIBRARY: cDNA to mRNA
        (B) CLONE: 4C (ix) FEATURE:
        (A) NAME/KEY: mat_peptide
        (B) LOCATION: 282..1217

(ix) FEATURE:
        (A) NAME/KEY: CDS
        (B) LOCATION: 117..1220

(xi) SEQUENCE DESCRIPTION: SEQ ID NO:3:

```
CCTTCAAAAC CACTTGTTTC TTCAGTTCCA CTCTGCTTCT TCCCCTTTCT CTTCTCATAC      60

TCACCCAGCT TTCCTTTTTA TTAAAAAACA AAAAAAAATG TTGAAGCTTT CGTGCA         116
```

| | | | | | | | | | | | | | | | | |
|---|---|---|---|---|---|---|---|---|---|---|---|---|---|---|---|---|
| ATG | GCT | TGG | ACC | GGG | CTC | ATA | TGC | TGG | CCC | AAT | GCG | TTT | GCG | GGC | CGG | 164 |
| Met | Ala | Trp | Thr | Gly | Leu | Ile | Cys | Trp | Pro | Asn | Ala | Phe | Ala | Gly | Arg | |
| -55 | | | | -50 | | | | -45 | | | | | | | -40 | |
| GGC | CGC | TGC | GCT | CGT | CCC | AGC | CGG | AGG | ATA | AGC | GGC | ATC | TCC | GGA | TTC | 212 |
| Gly | Arg | Cys | Ala | Arg | Pro | Ser | Arg | Arg | Ile | Ser | Gly | Ile | Ser | Gly | Phe | |
| | | | -35 | | | | | -30 | | | | | | -25 | | |
| TGG | TCC | CCG | GAA | GGA | GGG | CGG | ATC | CGG | GTG | TCG | GCG | GTG | GTG | TCG | GCG | 260 |
| Trp | Ser | Pro | Glu | Gly | Gly | Arg | Ile | Arg | Val | Ser | Ala | Val | Val | Ser | Ala | |
| | | -20 | | | | | | -15 | | | | | -10 | | | |
| AAG | GAT | GGC | GCG | GTG | GCG | ACC | CGG | GTG | GAG | GCG | GAG | TCC | GGG | ACG | CTG | 308 |
| Lys | Asp | Gly | Ala | Val | Ala | Thr | Arg | Val | Glu | Ala | Glu | Ser | Gly | Thr | Leu | |
| | | -5 | | | | | 1 | | | | 5 | | | | | |
| GCG | GAC | CGG | CTG | AGG | GTG | GGG | AGC | TTG | ACG | GAG | GAT | GGG | TTG | TCT | TAC | 356 |
| Ala | Asp | Arg | Leu | Arg | Val | Gly | Ser | Leu | Thr | Glu | Asp | Gly | Leu | Ser | Tyr | |
| 10 | | | | | 15 | | | | | 20 | | | | | 25 | |
| AAG | GAG | AAG | TTC | ATT | GTG | AGG | AGC | TAC | GAA | GTT | GGG | ATC | AAT | AAG | ACT | 404 |
| Lys | Glu | Lys | Phe | Ile | Val | Arg | Ser | Tyr | Glu | Val | Gly | Ile | Asn | Lys | Thr | |
| | | | | 30 | | | | | 35 | | | | | 40 | | |
| GCC | ACT | GTT | GAA | ACC | ATT | GCT | AAT | CTC | TTG | CAG | GAG | GTT | GGA | TGT | AAT | 452 |
| Ala | Thr | Val | Glu | Thr | Ile | Ala | Asn | Leu | Leu | Gln | Glu | Val | Gly | Cys | Asn | |
| | | | 45 | | | | | 50 | | | | | 55 | | | |
| CAT | GCT | CAG | AGT | GTT | GGA | TAT | TCT | ACT | GAT | GGT | TTT | GCA | ACC | ACC | CCT | 500 |
| His | Ala | Gln | Ser | Val | Gly | Tyr | Ser | Thr | Asp | Gly | Phe | Ala | Thr | Thr | Pro | |
| | | 60 | | | | | 65 | | | | | 70 | | | | |
| ACG | ATG | AGA | AAA | TTG | CGT | CTC | ATA | TGG | GTT | ACT | GCT | CGC | ATG | CAC | ATT | 548 |
| Thr | Met | Arg | Lys | Leu | Arg | Leu | Ile | Trp | Val | Thr | Ala | Arg | Met | His | Ile | |
| | 75 | | | | | 80 | | | | | 85 | | | | | |
| GAA | ATC | TAC | AAA | TAC | CCT | GCT | TGG | AGT | GAC | GTT | GTT | GAG | ATA | GAG | ACA | 596 |
| Glu | Ile | Tyr | Lys | Tyr | Pro | Ala | Trp | Ser | Asp | Val | Val | Glu | Ile | Glu | Thr | |
| 90 | | | | | 95 | | | | | 100 | | | | | 105 | |
| TGG | TGC | CAA | GGT | GAA | GGA | AGG | GTT | GGG | ACA | AGG | CGT | GAT | TTT | ATA | CTG | 644 |
| Trp | Cys | Gln | Gly | Glu | Gly | Arg | Val | Gly | Thr | Arg | Arg | Asp | Phe | Ile | Leu | |
| | | | | 110 | | | | | 115 | | | | | 120 | | |
| AAA | GAC | TAT | GCA | AGT | GAT | GCA | GTC | ATT | GGA | AGG | GCA | ACA | AGC | AAA | TGG | 692 |
| Lys | Asp | Tyr | Ala | Ser | Asp | Ala | Val | Ile | Gly | Arg | Ala | Thr | Ser | Lys | Trp | |
| | | | 125 | | | | | 130 | | | | | 135 | | | |
| GTA | ATG | ATG | AAT | CAG | GAC | ACC | AGA | CGA | CTC | CAG | AAA | GTT | TCT | GAT | GAT | 740 |
| Val | Met | Met | Asn | Gln | Asp | Thr | Arg | Arg | Leu | Gln | Lys | Val | Ser | Asp | Asp | |
| | | 140 | | | | | 145 | | | | | 150 | | | | |
| GTT | AAA | GAA | GAG | TAT | TTG | GTT | TTC | TGT | CCT | CGA | GAG | CCC | AGG | TTA | GCA | 788 |
| Val | Lys | Glu | Glu | Tyr | Leu | Val | Phe | Cys | Pro | Arg | Glu | Pro | Arg | Leu | Ala | |
| | 155 | | | | | 160 | | | | | 165 | | | | | |
| ATT | CCA | GAG | GCA | GAT | AGC | AAT | AAC | TTG | AAG | AAA | ATA | CCG | AAA | TTG | GAA | 836 |
| Ile | Pro | Glu | Ala | Asp | Ser | Asn | Asn | Leu | Lys | Lys | Ile | Pro | Lys | Leu | Glu | |
| 170 | | | | | 175 | | | | | 180 | | | | | 185 | |
| GAC | CCT | GCC | CAG | TAT | TCC | AGA | CTT | GGA | CTT | GTG | CCA | AGA | AGA | GCG | GAT | 884 |
| Asp | Pro | Ala | Gln | Tyr | Ser | Arg | Leu | Gly | Leu | Val | Pro | Arg | Arg | Ala | Asp | |
| | | | 190 | | | | | 195 | | | | | 200 | | | |
| CTG | GAC | ATG | AAT | CAG | CAT | GTT | AAC | AAT | GTC | ACC | TAT | ATT | GGA | TGG | GTG | 932 |
| Leu | Asp | Met | Asn | Gln | His | Val | Asn | Asn | Val | Thr | Tyr | Ile | Gly | Trp | Val | |
| | | | 205 | | | | | 210 | | | | | 215 | | | |
| CTT | GAG | AGC | ATG | CCT | CAA | GAA | ATC | ATT | GAT | AGT | CAT | GAG | TTG | CAG | AGT | 980 |
| Leu | Glu | Ser | Met | Pro | Gln | Glu | Ile | Ile | Asp | Ser | His | Glu | Leu | Gln | Ser | |
| | | | 220 | | | | | 225 | | | | | 230 | | | |
| ATT | ACC | TTG | GAT | TAC | AGA | CGA | GAG | TGC | GGA | CAG | CAT | GAC | ATA | GTT | GAT | 1028 |
| Ile | Thr | Leu | Asp | Tyr | Arg | Arg | Glu | Cys | Gly | Gln | His | Asp | Ile | Val | Asp | |
| | | 235 | | | | | 240 | | | | | 245 | | | | |
| TCC | CTC | ACT | AGT | GTG | GAA | GAA | ATC | CAG | GGT | GGT | GCC | GAG | GCA | GTT | TCA | 1076 |
| Ser | Leu | Thr | Ser | Val | Glu | Glu | Ile | Gln | Gly | Gly | Ala | Glu | Ala | Val | Ser | |
| 250 | | | | | 255 | | | | | 260 | | | | | 265 | |

| | | | | | | | | | | | | | | | | |
|---|---|---|---|---|---|---|---|---|---|---|---|---|---|---|---|---|
| GAA | CTG | AAA | AGT | ACA | AAT | GGA | TCT | GCC | ATG | GCA | AGG | GAA | GAC | AAA | CAT | 1124 |
| Glu | Leu | Lys | Ser | Thr | Asn | Gly | Ser | Ala | Met | Ala | Arg | Glu | Asp | Lys | His | |
| | | | 270 | | | | | | 275 | | | | | 280 | | |
| GAA | CAC | CAG | CAG | TTT | CTG | CAT | CTA | CTT | AGG | TTG | TCT | ACT | GAA | GGA | CTT | 1172 |
| Glu | His | Gln | Gln | Phe | Leu | His | Leu | Leu | Arg | Leu | Ser | Thr | Glu | Gly | Leu | |
| | | | 285 | | | | | 290 | | | | | 295 | | | |
| GAG | ATA | AAC | CGG | GGA | CGA | ACG | GAA | TGG | AGA | AAG | AAA | GCT | CCA | AGA | | |
| Glu | Ile | Asn | Arg | Gly | Arg | Thr | Glu | Trp | Arg | Lys | Lys | Ala | Pro | Arg | | |
| | | 300 | | | | | 305 | | | | 310 | | | | | |

```
                                                              TGAGAACCAT   1227
TACGTGTGCT  TCCACCCAAA  TCCATGATTC  TGTTTTTGTC  TTTCTTGTGT  TGTTTCACGT   1287
TACCAGGGTT  ATGAACTTAT  CAATTTTCCC  TTTATATTTT  GCTTAGAGTT  TGTGGACCCT   1347
TAATAGGGGA  TTGGAGGAGT  TAAAATTTTG  TCGCTGTTTT  CTTGTCATGC  TCACAAATTT   1407
AAATTGTTGG  AATTCATCAT  CAAGCTTATC  GATACCGTCG  ACCTCGAGGG  GGGGCCCGGT   1467
ACCCAATTC                                                                1476
```

( 2 ) INFORMATION FOR SEQ ID NO:4:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ala | Trp | Thr | Gly | Leu | Ile | Cys | Trp | Pro | Asn | Ala | Phe | Ala | Gly | Arg |
| -55 | | | | | -50 | | | | -45 | | | | | | -40 |
| Gly | Arg | Cys | Ala | Arg | Pro | Ser | Arg | Arg | Ile | Ser | Gly | Ile | Ser | Gly | Phe |
| | | | | -35 | | | | | -30 | | | | | -25 | |
| Trp | Ser | Pro | Glu | Gly | Gly | Arg | Ile | Arg | Val | Ser | Ala | Val | Val | Ser | Ala |
| | | | -20 | | | | | -15 | | | | | -10 | | |
| Lys | Asp | Gly | Ala | Val | Ala | Thr | Arg | Val | Glu | Ala | Glu | Ser | Gly | Thr | Leu |
| | | -5 | | | | | 1 | | | | 5 | | | | |
| Ala | Asp | Arg | Leu | Arg | Val | Gly | Ser | Leu | Thr | Glu | Asp | Gly | Leu | Ser | Tyr |
| 10 | | | | | 15 | | | | 20 | | | | | | 25 |
| Lys | Glu | Lys | Phe | Ile | Val | Arg | Ser | Tyr | Glu | Val | Gly | Ile | Asn | Lys | Thr |
| | | | | 30 | | | | | 35 | | | | | 40 | |
| Ala | Thr | Val | Glu | Thr | Ile | Ala | Asn | Leu | Leu | Gln | Glu | Val | Gly | Cys | Asn |
| | | | 45 | | | | | 50 | | | | | 55 | | |
| His | Ala | Gln | Ser | Val | Gly | Tyr | Ser | Thr | Asp | Gly | Phe | Ala | Thr | Thr | Pro |
| | | 60 | | | | | 65 | | | | | 70 | | | |
| Thr | Met | Arg | Lys | Leu | Arg | Leu | Ile | Trp | Val | Thr | Ala | Arg | Met | His | Ile |
| | 75 | | | | | 80 | | | | | 85 | | | | |
| Glu | Ile | Tyr | Lys | Tyr | Pro | Ala | Trp | Ser | Asp | Val | Val | Glu | Ile | Glu | Thr |
| 90 | | | | | 95 | | | | | 100 | | | | | 105 |
| Trp | Cys | Gln | Gly | Glu | Gly | Arg | Val | Gly | Thr | Arg | Arg | Asp | Phe | Ile | Leu |
| | | | | 110 | | | | | 115 | | | | | 120 | |
| Lys | Asp | Tyr | Ala | Ser | Asp | Ala | Val | Ile | Gly | Arg | Ala | Thr | Ser | Lys | Trp |
| | | | 125 | | | | | 130 | | | | | 135 | | |
| Val | Met | Met | Asn | Gln | Asp | Thr | Arg | Arg | Leu | Gln | Lys | Val | Ser | Asp | Asp |
| | | 140 | | | | | 145 | | | | | 150 | | | |
| Val | Lys | Glu | Glu | Tyr | Leu | Val | Phe | Cys | Pro | Arg | Glu | Pro | Arg | Leu | Ala |
| | 155 | | | | | 160 | | | | | 165 | | | | |
| Ile | Pro | Glu | Ala | Asp | Ser | Asn | Asn | Leu | Lys | Lys | Ile | Pro | Lys | Leu | Glu |

| 170 | | | | | 175 | | | | | 180 | | | | | 185 |
|---|---|---|---|---|---|---|---|---|---|---|---|---|---|---|---|
| Asp | Pro | Ala | Gln | Tyr | Ser | Arg | Leu | Gly | Leu | Val | Pro | Arg | Arg | Ala | Asp |
| | | | | 190 | | | | | 195 | | | | | 200 | |
| Leu | Asp | Met | Asn | Gln | His | Val | Asn | Asn | Val | Thr | Tyr | Ile | Gly | Trp | Val |
| | | | 205 | | | | | 210 | | | | | 215 | | |
| Leu | Glu | Ser | Met | Pro | Gln | Glu | Ile | Ile | Asp | Ser | His | Leu | Gln | Ser | |
| | | 220 | | | | | 225 | | | | | 230 | | | |
| Ile | Thr | Leu | Asp | Tyr | Arg | Arg | Glu | Cys | Gly | Gln | His | Asp | Ile | Val | Asp |
| | 235 | | | | | 240 | | | | | 245 | | | | |
| Ser | Leu | Thr | Ser | Val | Glu | Glu | Ile | Gln | Gly | Gly | Ala | Glu | Ala | Val | Ser |
| 250 | | | | | 255 | | | | | 260 | | | | | 265 |
| Glu | Leu | Lys | Ser | Thr | Asn | Gly | Ser | Ala | Met | Ala | Arg | Glu | Asp | Lys | His |
| | | | | 270 | | | | | 275 | | | | | 280 | |
| Glu | His | Gln | Gln | Phe | Leu | His | Leu | Leu | Arg | Leu | Ser | Thr | Glu | Gly | Leu |
| | | | 285 | | | | | 290 | | | | | 295 | | |
| Glu | Ile | Asn | Arg | Gly | Arg | Thr | Glu | Trp | Arg | Lys | Lys | Ala | Pro | Arg | |
| | | | 300 | | | | | 305 | | | | | 310 | | |

(2) INFORMATION FOR SEQ ID NO:5:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:5:

| Arg | Val | Glu | Ala | Pro | Gly | Gly | Thr | Leu | Ala | Asp | Arg | Leu |
|---|---|---|---|---|---|---|---|---|---|---|---|---|
| 1 | | | | 5 | | | | | 10 | | | |

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

| Ile | Glu | Ile | Tyr | Lys | Tyr | Pro | Ala | Trp | Leu | Asp | Ile | Val | Glu | Ile |
|---|---|---|---|---|---|---|---|---|---|---|---|---|---|---|
| 1 | | | | 5 | | | | | 10 | | | | | 15 |

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:7:

| Val | Glu | Ala | Pro | Gly | Gly | Thr | Leu | Ala | Asp |
|---|---|---|---|---|---|---|---|---|---|
| 1 | | | | 5 | | | | | 10 |

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (  i i  ) MOLECULE TYPE: DNA (  x i  ) SEQUENCE DESCRIPTION: SEQ ID NO:8:

GTKGARGCNC  CWGGWGGNAC  NYTKGCAKA                                                                29

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 15
        ( C ) IDENTIFICATION METHOD: experimental
        ( D ) OTHER INFORMATION: /evidence=EXPERIMENTAL
            / mod_base=i ( i x ) FEATURE:
        ( A ) NAME/KEY: modified_base
        ( B ) LOCATION: 9
        ( C ) IDENTIFICATION METHOD: experimental
        ( D ) OTHER INFORMATION: /evidence=EXPERIMENTAL
            / mod_base=i ( i x ) FEATURE:
        ( A ) NAME/KEY: modified_base
        ( B ) LOCATION: 18
        ( C ) IDENTIFICATION METHOD: experimental
        ( D ) OTHER INFORMATION: /evidence=EXPERIMENTAL
            / mod_base=i ( i x ) FEATURE:
        ( A ) NAME/KEY: modified_base
        ( B ) LOCATION: 21
        ( C ) IDENTIFICATION METHOD: experimental
        ( D ) OTHER INFORMATION: /evidence=EXPERIMENTAL
            / mod_base=i ( x i ) SEQUENCE DESCRIPTION: SEQ ID NO:9:

GTKGARGCNC  CWGGNGGNAC  NYTKGCAKA                                                                29

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Ile  Glu  Ile  Tyr  Lys  Tyr  Pro  Ala  Trp  Leu  Asp  Ile  Glu  Ile
 1                  5                        10

( 2 ) INFORMATION FOR SEQ ID NO:11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

ATNGARATNT  AYAARTAYCC  NKCNTGGYTN  GAYATNGARA  TN                                                42

( 2 ) INFORMATION FOR SEQ ID NO:12:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: modified_base
( B ) LOCATION: 3
( C ) IDENTIFICATION METHOD: experimental
( D ) OTHER INFORMATION: /evidence=EXPERIMENTAL
/ mod_base=i ( i x ) FEATURE:
( A ) NAME/KEY: modified_base
( B ) LOCATION: 9
( C ) IDENTIFICATION METHOD: experimental
( D ) OTHER INFORMATION: /evidence=EXPERIMENTAL
/ mod_base=i ( i x ) FEATURE:
( A ) NAME/KEY: modified_base
( B ) LOCATION: 21
( C ) IDENTIFICATION METHOD: experimental
( D ) OTHER INFORMATION: /evidence=EXPERIMENTAL
/ mod_base=i ( i x ) FEATURE:
( A ) NAME/KEY: modified_base
( B ) LOCATION: 24
( C ) IDENTIFICATION METHOD: experimental
( D ) OTHER INFORMATION: /evidence=EXPERIMENTAL
/ mod_base=i ( i x ) FEATURE:
( A ) NAME/KEY: modified_base
( B ) LOCATION: 30
( C ) IDENTIFICATION METHOD: experimental
( D ) OTHER INFORMATION: /evidence=EXPERIMENTAL
/ mod_base=i ( i x ) FEATURE:
( A ) NAME/KEY: modified_base
( B ) LOCATION: 36
( C ) IDENTIFICATION METHOD: experimental
( D ) OTHER INFORMATION: /evidence=EXPERIMENTAL
/ mod_base=i ( x i ) SEQUENCE DESCRIPTION: SEQ ID NO:12:

ATNGARATNT ATAARTATCC NGCNTGGTTN GATATNGARA T       41

( 2 ) INFORMATION FOR SEQ ID NO:13:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:13:

GTGTGGAAGC GATACAGGGT GGTGCCGAGG C       31

( 2 ) INFORMATION FOR SEQ ID NO:14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear

61

62
-continued ( i i ) MOLECULE TYPE: DNA ( x i ) SEQUENCE DESCRIPTION: SEQ ID NO:14:

TAYAARGARA ARTTY                                                    15

( 2 ) INFORMATION FOR SEQ ID NO:15:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:15:

AARTGGGTNA TGATGAAYCA A                                    21

( 2 ) INFORMATION FOR SEQ ID NO:16:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:16:

YTGRTTCATC ATNACCCAYT T                                    21

( 2 ) INFORMATION FOR SEQ ID NO:17:

( i ) SEQUENCE CHARACTERISTICS:
           ( A ) LENGTH: 24 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:17:

YTGYTGRTGY TCRTGYTTMT CYTC                              24

( 2 ) INFORMATION FOR SEQ ID NO:18:

( i ) SEQUENCE CHARACTERISTICS:
           ( A ) LENGTH: 35 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:18:

AAAAATCTAG AAGCTTTCGT GCCATGGCTT GGACC                 35

( 2 ) INFORMATION FOR SEQ ID NO:19:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:19:

AGCGTACCGG GATCCGCCTC TA                                  22

( 2 ) INFORMATION FOR SEQ ID NO:20:

( i ) SEQUENCE CHARACTERISTICS:
    ( A ) LENGTH: 1378 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Brassica napus ( x i ) SEQUENCE DESCRIPTION: SEQ ID NO:20:

```
ATGACCATGA  TTACGCCAAG  CTCGAAATTA  ACCCTCACTA  AAGGGAACAA  AAGCTGGAGC    60
TCCACCGCGG  TGGCGGCCGC  TCTAGAACTA  GTGGATCCCC  CGGGCTGCAG  GAATTCGGCA   120
CGAGAAGAAC  TTTGTTGTTC  GTTTGATGTA  GGTTAGGAGG  TGGGATGTAA  TCAGTTTCAG   180
AGCGTTGTAT  TTTTGACTGA  TGGGTTTGCG  ACAACACCTA  CCATGAGGAA  ACTGAATCTC   240
ATTTGGGTCA  CTTCGAGAAT  GCACATTGAG  ATCTACAGAT  ATCCAGCTTG  GTATTGTTTT   300
TTTTTTTTCT  TTTTGGCTGC  GTATGTTTTG  ATGACAACAA  ATGAGTTGAA  TTCTTAAAAA   360
TTTTGGTTAC  AGGGGTGATG  TGGTTGTCAG  AGTGAAGAAG  GATAGCGACA  AGGCGTGACT   420
GGATTCTTAA  GGACATTGCT  AACCGGCGAA  TTCACTGGCC  GCAGTACTAG  GTTTCCTTCT   480
CATCATTGTT  TGCTTTCTCC  ATTGGTTTGT  GCAATGGAAT  AAAATTTTCT  TATGTTAAAG   540
ATATAAGTTT  CTGTCACTTG  GGTTTATGGG  ACTGTCCTGA  TTAGTTGTAC  CTATGTGTTA   600
CCGTTTCAGC  AAGTAGGTGA  TGATGAACCA  AGACACAAGA  CGGCTACAGA  AAGTTTCTGA   660
TGATGTTCGG  GACGAGCACT  TGATGTTTTG  TCCTAAAGAA  CCCAGGTAAA  AGAACTTTGT   720
GCCAATGCAA  TGTTTGCTGG  TCAATCATAT  CGTTATATTC  ATGAATTGCC  AACTATTCTG   780
TTTATTGTAT  ATCTTTGTAG  ATTAGCATAT  CCTGAGGAGG  AAAATACCAG  AAGCTTGAAG   840
AATATCCCCA  AACTCGAAGA  TCTGGCCAAG  TACTCAATCA  TTGGACTTAA  GGTATAAAAT   900
AGAACAATAA  GATTCTTTGT  AAGAATCAAC  ATTCCTAAAG  GACTTTATAA  TCATGTTTCT   960
TTGCAGCCAA  GAGCGAGCTG  ATCTCGGCAT  GAACCATCAT  GTCAATAATG  TCACATATAT  1020
TGGATGGCTT  CTTGAGGTTA  GTGTCATCAT  CAGCTTCAGT  AATAATCATA  TGAGCATACC  1080
TCAAGAGTTA  TAGACACGCA  CGAACTTCAG  GTCATAACTT  TGGATTACAG  ACGAGAATTT  1140
AGCAAGACGA  TGTGGTGGAT  TCATTGACCA  CCTCAAAGAA  TGGCTCTGCA  ACATCAGGCA  1200
CACAAAGCCA  CAACAATACC  CAGTTCTTAC  ATCTCCTAAG  GTTGTAGGTT  GAAAGAACTA  1260
TGAAGTGGTG  AGCTGCAGAT  CTTTGCATGT  GCAGAGGGTT  GTAGGTGGGG  GCCTTAGCAG  1320
GGAGGTGTAC  GTTGTGTCAT  TGAATAACTC  GAGGGGGGGC  CCGGTACCCA  ATTCGCCC    1378
```

( 2 ) INFORMATION FOR SEQ ID NO:21:

( i ) SEQUENCE CHARACTERISTICS:
    ( A ) LENGTH: 852 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Cuphea lanceolata ( x i ) SEQUENCE DESCRIPTION: SEQ ID NO:21:

```
CCCCCGGGCT  GCAGGAATTC  GATTACAAGG  AGAAATTCAT  TGTAAGATGC  TACGAGGTCG    60
```

```
GTATTAACAA GACAGCCACC GTCGAGACCA TGGCAAATCT TTTGCAGGTC TCTTTCTTGC        120

ATGCATGCAT CGTCAGGTTT CTGGGCATTG GTGATTTGCT TGTATTAATT TACATGTCAA        180

ATTTAATATT TCCTTGTCTC CGACATGCAA CACCATTTTT TTTTCTTTAA ATGTTCACTT        240

TGGATACAGG AAGTAGGTTG TAACCATGCT CAGAGTATTG GATTCTCAAC CGATGGTTTT        300

GCGACGACCA CTACCATGAG AAAATTGAAT CTGATATGGG TTACTCGTCG AATGCACATA        360

GAAATTTACA AGTACCCAGC ATGGTTAGTT AGTTCTTTCC ACTCTCTTTC TTCATCTCCC        420

CAGCCACCCC ACTGCTAACT TTTTGATTGA CAATTGTTGA TACGTACTCT AGGGGTGATG        480

TGGTTGAAAT TGAGACTTGG TGCCAAAGTG AAGGAAGAAT TGGAACAAGA AGGGATTGGA        540

TTCTCAAGGA CTATGCTAAT GGTGATGTTA TTGGAAGAGC CACAAGGTAG ACAGACTGCT        600

CTCTCATATA TACAGCAGTG AGAGAACAAA AGAATAATAT TGGAACAATA TCAAATCGAA        660

TCTAAACAAT TGGAAGACAT TATTTTGAGG AAAGGGAAGA TTGAAACTGA TGTTCTTAGT        720

AATCTATACG TGCACGGCGC CATGATTATC CATTTCATGA GAATTGTTCC AATCATTTAT        780

ATTAATCTGT TTTCAGCAAG TGGGTCATGA TGAATCAAAT CAAGCTTATC GATACCGTCG        840

ACCTCGAGGG GG                                                            852
```

( 2 ) INFORMATION FOR SEQ ID NO:22:

( i ) SEQUENCE CHARACTERISTICS:
        ( A ) LENGTH: 865 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Cuphea viscosissima ( x i ) SEQUENCE DESCRIPTION: SEQ ID NO:22:

```
CCCCCTCGAG GTCGACGGTA TCGATAAGCT TGATTATAAG GAGAAGTTTA TTGTCAGATG         60

CTACGAGGTC GGTATTAACA AGACAGCCAC CGTCGAGACC ATGGCAAATC TTTTGCAGGT        120

CAGGTTCTCT CTGTTTCCAT ATCGTTGCAT GCATGCATCG GTTTCTGGGC ATTGGTTATT        180

TGCTTGTATT AATTTACATG TCAAAATTTA ATTTAATATT TCCTTGTCTC CGACATGCAA        240

CACCATTTTT TTTTTTAAAT GTTCACTTTC AATGCAGGAA GTAGGTTGTA ACCATGCTCA        300

GAGTCTTGGA TTCTCAACCG ATGGTTTTGC GACGACCACT ACCATGAGGA AATTGAATCT        360

GATATGGGTT ACTGCTCGAA TGCACATAGA AATTTACAAG TACCCAGCAT GGTTAGTTAG        420

TTCTTCCACT CTCTTTTCTT CATCTCCCCA GCCACCCCAC TGCACTTTTT GATTGACAAT        480

TGTTGGATAC GTCTCTAGGG GTGATGTGGT TGAAATTGAG ACTTGGTGCC AAAGTGAAGG        540

AAGAATCGGA ACAAGAAGGG ATTGGATTCT CAAGGACTAT GCTAATGGTG AAGTTATTGG        600

AAGAGCCACA AGGTAGACAG ACTGCTCTCA TATATACATC AGTGAGATAA CAAAGGGAAT        660

AATATTGGAA CAATATCAAA TCGAATCTAA ACAATTGGAA GACATTATTT TGAGCAAGTG        720

AAGATTGAAA CTGATGTTCT TAGTAATCTA TACGTGCACG GCGCCATGAT TATCCATTTC        780

ATGAGAATTG TTCCAATCAT TTATATTAAT CTGTTTTCAG CAAATGGGTG ATGATGAACC        840

AAATCGAATT CCTGCAGCCC GGGGG                                              865
```